United States Patent [19]

Karanewsky et al.

[11] Patent Number: 4,904,646
[45] Date of Patent: Feb. 27, 1990

[54] PHOSPHORUS-CONTAINING HMG-COA REDUCTASE INHIBITORS

[75] Inventors: Donald S. Karanewsky, East Windsor; Scott A. Biller, Ewing; Eric M. Gordon, Pennington, all of N.J.

[73] Assignee: E. R. Squibb & Sons, Inc., Princeton, N.J.

[21] Appl. No.: 182,696

[22] Filed: Apr. 18, 1988

Related U.S. Application Data

[63] Continuation-in-part of Ser. No. 109,680, Oct. 19, 1987, abandoned, which is a continuation-in-part of Ser. No. 53,281, May 22, 1987, abandoned.

[51] Int. Cl.[4] .................. A61K 31/66; C07F 9/30; C07F 9/32
[52] U.S. Cl. .................. 514/120; 558/179; 560/102; 562/24; 562/492; 562/493
[58] Field of Search .................. 558/179; 514/120; 562/24, 492, 493; 560/102

[56] References Cited

U.S. PATENT DOCUMENTS

| | | | |
|---|---|---|---|
| 3,983,140 | 9/1976 | Endo et al. | 260/343.5 |
| 4,049,495 | 9/1977 | Endo et al. | 195/36 |
| 4,137,322 | 1/1979 | Endo et al. | 424/273 |
| 4,375,475 | 3/1983 | Willard et al. | 424/279 |
| 4,399,287 | 8/1983 | Baillie et al. | 558/179 |

FOREIGN PATENT DOCUMENTS

| | | |
|---|---|---|
| 127848A | 5/1984 | European Pat. Off. |
| 8402131 | 6/1984 | European Pat. Off. |
| 8402903 | 8/1984 | European Pat. Off. |
| 142146A | 11/1984 | European Pat. Off. |
| 127848 | 12/1984 | European Pat. Off. |
| 0164698 | 6/1985 | European Pat. Off. |
| 142146 | 6/1986 | European Pat. Off. |
| 2596393A1 | 4/1986 | France. |
| 2596393 | 10/1987 | France. |
| 1586152 | 5/1978 | United Kingdom. |
| 2162179 | 7/1985 | United Kingdom. |

OTHER PUBLICATIONS

Singer et al., Proc. Soc. Exper. Biol. Med., 102, 370 (1982), "New Inhibitors of in vitro Conversion of Acetate and Mevalonate to Cholesterol".
Hulcher, Arch. Biochem. Biophys., 146, 422 (1971), "Inhibition of Hepatic Cholesterol Biosynthesis by 3,5-Dihydroxy-3,4,4-Trimethylvaleric Acid and Its Site of Action".
Brown et al., J. Chem. Soc. Perkin I., 1165 (1976), "Crystal and Molecular Structure of compactin, A New Antifungal Metabolite from Penicillium breviocompactum".
Anderson, P., Ger. Offen. DE 3,525,256, "Naphthyl Analogs of Mevalonolactones and Their Derivatives".

Primary Examiner—Anton H. Sutto
Attorney, Agent, or Firm—Burton Rodney

[57] ABSTRACT

Compounds which are useful as inhibitors of cholesterol biosynthesis and thus as hypocholesterolemic agents are provided which have the structure

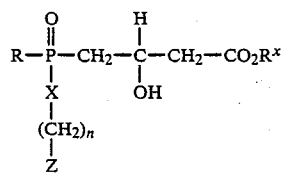

including salts thereof, wherein R is OH, lower alkoxy or lower alkyl;
$R^x$ is H or alkyl;
X is —O— or —NH—;
n is 1 or 2
Z is a hydrophobic anchor, such as

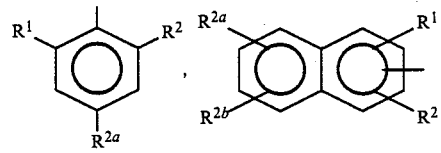

or

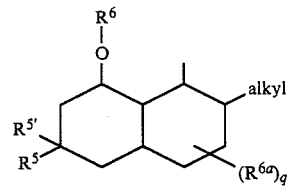

wherein the dotted lines represent optional double bonds.

New intermediates used in preparing the above compounds, pharmaceutical compositions containing such compounds and a method for using such compounds to inhibit cholesterol biosynthesis are also provided.

22 Claims, No Drawings

PHOSPHORUS-CONTAINING HMG-COA REDUCTASE INHIBITORS

REFERENCE TO OTHER APPLICATIONS

This application is a continuation-in-part of application Ser. No. 109,680, filed Oct. 19, 1987 which is a continuation-in-part of application Ser. No. 053,281, filed May 22, 1987, both now abandoned.

FIELD OF THE INVENTION

The present invention relates to new phosphorus-containing compounds which inhibit the activity of 3-hydroxy-3-methylglutaryl-coenzyme A reductase and thus is useful in inhibiting cholesterol biosynthesis, to hypocholesterolemic compositions containing such compounds, to new intermediates formed in the preparation of such compounds and to a method of using such compounds for such purposes.

BACKGROUND OF THE INVENTION

F. M. Singer et al., *Proc. Soc. Exper. Biol. Med.*, 102, 370 (1959) and F. H. Hulcher, *Arch. Biochem. Biophys.*, 146, 422 (1971) disclose that certain mevalonate derivatives inhibit the biosynthesis of cholesterol.

Endo et al in U.S. Pat. Nos. 4,049,495, 4,137,322 and 3,983,140 disclose a fermentation product which is active in the inhibition of cholesterol biosynthesis. This product is called compactin and was reported by Brown et al., (*J. Chem. Soc. Perkin I.* 1165 (1976) to have a complex mevalonolactone structure.

GB 1,586,152 discloses a group of synthetic compounds of the formula

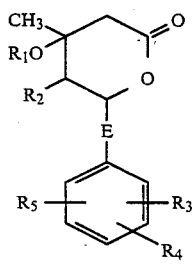

in which E represents a direct bond, $C_{1-3}$ alkylene bridge or a vinylene bridge and the various R's represent a variety of substituents.

The activity reported in the U.K. patent is less than 1% that of compactin.

U.S. Pat. No. 4,375,475 to Willard et al discloses hypocholesterolemic and hypolipemic compounds having the structure

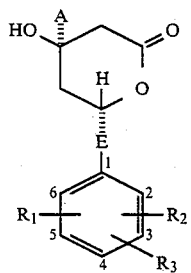

wherein A is H or methyl; E is a direct bond, $-CH_2-$, $-CH_2-CH_2-$, $-CH_2-CH_2-CH_2-$ or $-CH=CH-$; $R_1$, $R_2$ and $R_3$ are each selected from H, halogen, $C_{1-4}$ alkyl, $C_{1-4}$ haloalkyl, phenyl, phenyl substituted by halogen, $C_{1-4}$ alkoxy, $C_{2-8}$ alkanoyloxy, $C_{1-4}$ alkyl, or $C_{1-4}$ haloalkyl, and $OR_4$ in which $R_4$ is H, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$-alkyl, adamantyl-$C_{1-3}$-alkyl, or substituted phenyl $C_{1-3}$-alkyl in each of which the substituents are selected from halogen, $C_{1-4}$ alkoxy, $C_{1-4}$ alkyl, or $C_{1-4}$ haloalkyl; and the corresponding dihydroxy acids resulting from the hydrolytic opening of the lactone ring, and the pharmaceutically acceptable salts of said acids, and the $C_{1-3}$ alkyl and phenyl, dimethylamino or acetylamino substituted $C_{1-3}$-alkyl esters of the dihydroxy acids; all of the compounds being the enantiomers having a 4 R configuration in the tetrahydropyran moiety of the trans racemate shown in the above formula.

WO 84/02131 (PCT/EP83/00308) (based on U.S. application Ser. No. 443,668, filed Nov. 22, 1982, and U.S. application Ser. No. 548,850, filed Nov. 4, 1983), filed in the name of Sandoz AG discloses heterocyclic analogs of mevalono lactone and derivatives thereof having the structure

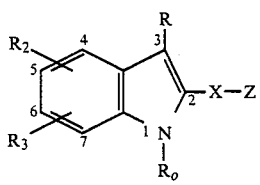

wherein one of R and $R_o$ is

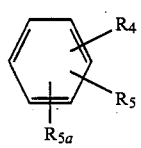

and the other is primary or secondary $C_{1-6}$ alkyl, $C_{3-6}$ cycloalkyl or phenyl—$(CH_2)_m$—, wherein $R_4$ is hydrogen, $C_{1-4}$ alkyl, $C_{1-4}$ alkoxy, (except t-butoxy), trifluoromethyl, fluoro, chloro, phenoxy or benzyloxy, $R_5$ is hydrogen, $C_{1-3}$ alkyl, $C_{1-3}$ alkoxy, trifluoromethyl, fluoro, chloro, phenoxy or benzyloxy, $R_{5a}$ is hydrogen, $C_{1-2}$ alkyl, $C_{1-2}$ alkoxy, fluoro or chloro, and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ trifluoromethyl, not more than one of $R_4$ and $R_5$ is phenoxy and not more than one of $R_4$ and $R_5$ is benzyloxy, $R_2$ is hydrogen, $C_{1-4}$ alkyl, $C_{3-6}$ cycloalkyl, $C_{1-4}$ alkoxy (except t-butoxy), trifluoromethyl, fluoro, chloro, phenoxy or benzyloxy, $R_3$ is hydrogen, $C_{1-3}$ alkyl, $C_{1-3}$ alkoxy, trifluoromethyl, fluoro, chloro, phenoxy or benzyloxy, with the provisos that $R_3$ must be hydrogen when $R_2$ is hydrogen, not more than one of $R_2$ and $R_3$ trifluoromethyl, not more than one of $R_2$ and $R_3$ is phenoxy, and not more than one of $R_2$ and $R_3$ is benzyloxy.

X is —(CH$_2$)$_n$— or —CH=CH— (n=0, 1, 2 or 3),
Z is

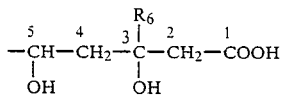  (II)

wherein R$_6$ is hydrogen or C$_{1-3}$ alkyl in free acid form or in the form of a physiologically-hydrolysable and -acceptable ester or a δ lactone thereof or in salt form.

GB 2162-179-A discloses naphthyl analogues of mevalolactone useful as cholesterol biosynthesis inhibitors having the structure

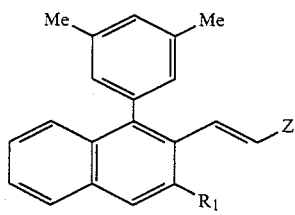

wherein R$_1$ = 1-3C alkyl;
Z is a gp. of formula Z$_1$ or Z$_2$:

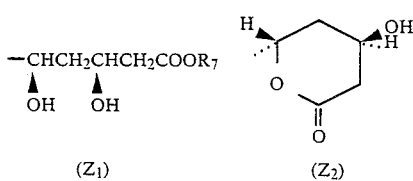

R$_7$ = H, a hydrolysable ester gp. or a cation.

European Pat. No. 164-698-A discloses preparation of lactones useful as anti-hypercholesterolemic agents by treating an amide with an organic sulphonyl halide R$^5$SO$_2$X, then removing the protecting group Pr.

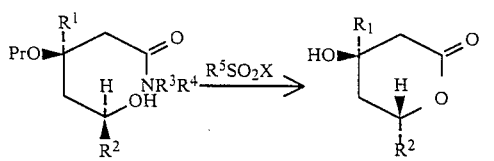

wherein
X = halo;
Pr = a carbinol-protecting group;
R$^1$ = H or CH$_3$;
R$^3$, R$^4$ = H, 1-3C alkyl or phenyl-(1-3C alkyl), the phenyl being optionally substituted by 1-3C alkyl, 1-3C alkoxy or halo;
R$^2$ = a group of formula (A) or (B):

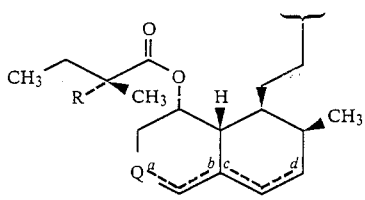  (A)

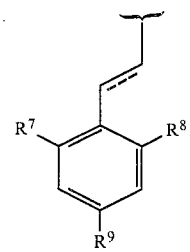  (B)

Q =

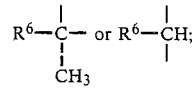

R$^6$ = H or OH;
R = H or CH$_3$;
a, b, c and d = optional double bonds;
R$^7$ = phenyl or benzyloxy, the ring in each case being optionally substituted by 1-3C alkyl or halo;
R$^8$, R$^9$ = 1-3C alkyl or halo;
R$^5$ = 1-3C alkyl, phenyl or mono- or di-(1-3C alkyl)-phenyl.

Anderson, Paul Leroy, Ger. Offen. DE3,525,256 discloses naphthyl analogs of mevalonolactones of the structure

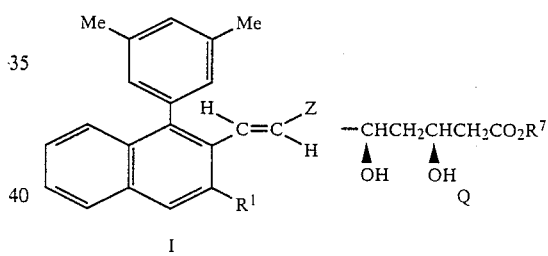

wherein R$^1$ is alkyl, Z = Q, Q$^1$; R$^7$ = H, or a hydrolyzable ester group useful as inhibitors of cholesterol biosynthesis and in treatment of atherosclerosis.

WO 8402-903 (based on U.S. application Ser. No. 460,600, filed Jan. 24, 1983) filed in the name of Sandoz AG discloses mevalono-lactone analogues useful as hypolipoproteinaemic agents having the structure

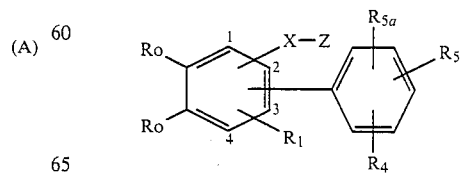  I wherein the two groups Ro together form a radical of formula

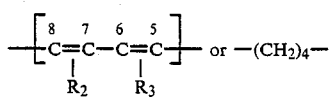

wherein $R_2$ is hydrogen, $C_{1-4}$ alkyl, $C_{1-4}$ alkoxy, (except t-butoxy), trifluoromethyl, fluoro, chloro, phenoxy or benzyloxy, $R_3$ is hydrogen, $C_{1-3}$ alkyl, $C_{1-3}$ alkoxy, trifluoromethyl, fluoro, chloro, phenoxy or benzyloxy, with the provisos that not more than one of $R_2$ and $R_3$ is trifluoromethyl, not more than one of $R_2$ and $R_3$ is phenoxy, and not more than one of $R_2$ and $R_3$ is benzyloxy, $R_1$ is hydrogen, $C_{1-6}$ alkyl, fluoro, chloro or benzyloxy, $R_4$ is hydrogen, $C_{1-4}$ alkyl, $C_{1-4}$ alkoxy, (except t-butoxy), trifluoromethyl, fluoro, chloro, phenoxy or benzyloxy, $R_5$ is hydrogen, $C_{1-3}$ alkyl, $C_{1-3}$ alkoxy, trifluoromethyl, fluoro, chloro, phenoxy or benzyloxy, $R_{5a}$ is hydrogen, $C_{1-2}$ alkyl, $C_{1-2}$ alkoxy, fluoro or chloro, and with the provisos that not more than one of $R_4$ and $R_5$ is trifluoromethyl, not more than one of $R_4$ and $R_5$ is phenoxy and not more than one of $R_4$ and $R_5$ is benzyloxy, X is

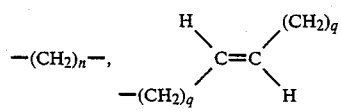

wherein n is 0, 1, 2 or 3 and both q's are 0 or one is 0 and the other is 1,

Z is

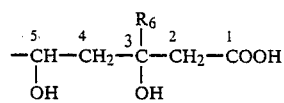

wherein $R_6$ is hydrogen or $C_{1-3}$ alkyl, with the general proviso that —X—Z and the $R_4$ bearing phenyl group are ortho to each other;
in free acid form or in the form of a physiologically-hydrolysable and acceptable ester or a δ lactone thereof or in salt form.

European patent application No. 127,848-A (Merck & Co, Inc.) discloses derivatives of 3-hydroxy-5-thia-ω-aryl-alkanoic acids having the structural formula:

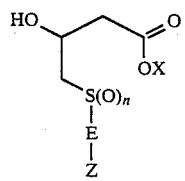

wherein Z is:

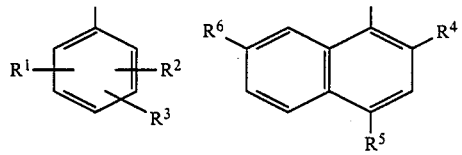

n is 0, 1 or 2;
E is —$CH_2$—, —$CH_2$—$CH_2$—, —$CH_2$—$CH_2$—$CH_2$—, —$CH=CH$—$CH_2$—; or —$CH_2$—$CH=CH$—;

$R_1$, $R_2$ and $R_3$ are, e.g., hydrogen, chloro, bromo, fluoro, $C_1$-alkyl, phenyl, substituted phenyl or $OR_7$ in which $R_7$ is, e.g., hydrogen, $C_{2-8}$alkanoyl, benzoyl, phenyl, substituted phenyl, $C_{1-9}$alkyl, cinnamyl, $C_{1-4}$haloalkyl, allyl, cycloalkyl-$C_{1-3}$alkyl, adamantyl-$C_{1-3}$-alkyl, or phenyl $C_{1-3}$ alkyl;

$R^4$, $R^5$ and $R^6$ are hydrogen, chloro, bromo, fluoro or $C_{1-3}$ alkyl; and X is, e.g., hydrogen, $C_{1-3}$ alkyl, a cation derived from an alkali metal or is ammonium.

Those compounds have antihypercholesterolemic activity by virtue of their ability to inhibit 3-hydroxy-3-methylglutaryl-coenzyme A (HMG-CoA) reductase and antifungal activity.

French patent application No. 2,596,393 A filed on Apr. 1, 1986 (Sanofi SA) discloses 3-carboxy-2-hydroxy-propane-phosphonic acid derivatives including salts thereof which are useful as hypolipaemic agents and have the formula:

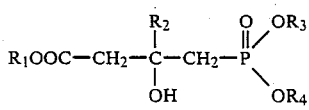

wherein
$R_1$ and $R_2$=H, lower alkyl or optionally substituted aralkyl;
$R_3$ and $R_4$=H, lower alkyl or optionally substituted aryl or aralkyl.

These compounds are disclosed as giving greater reductions in cholesterol, triglyceride and phospholipid levels than meglutol.

European patent application No. 142,146-A (Merck & Co., Inc) discloses mevinolin-like compounds of the structural formula:

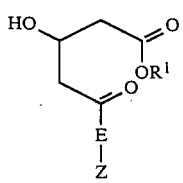

wherein:
$R^1$ is, e.g., hydrogen or $C_{1-4}$alkyl;
E is —$CH_2CH_2$, —$CH=CH$—, or —$(CH_2)_r$—; and
Z is

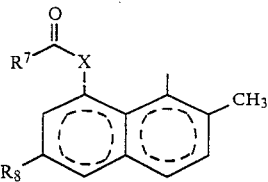 (1)

wherein
X is —O— or —NR$^9$ wherein R$^9$ is hydrogen or C$_{1-3}$alkyl;
R$^7$ is C$_{2-8}$alkyl; and
R$^8$ is hydrogen or CH$_3$;

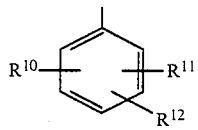 (2)

wherein R$^{10}$, R$^{11}$ and R$^{12}$ are independently, e.g., hydrogen, halogen or C$_{1-4}$alkyl;

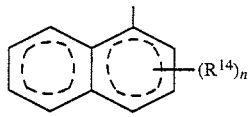 (3)

DESCRIPTION OF THE INVENTION

In accordance with the present invention, there is provided phosphorus-containing compounds which inhibit the enzyme 3-hydroxy-3-methylglutarylcoenzyme A reductase (HMG-CoA Reductase) and thus are useful as hypocholesterolemic agents and include the following moiety

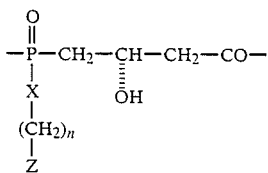

wherein X is —O— or —NH—, n is 1 or 2 and Z is a "hydrophobic anchor".

The term hydrophobic anchor as employed herein refers to a lipophilic group which when linked to the HMG-like upper side chain of the molecule by the appropriate linker ("X"), binds to a hydrophobic pocket of the enzyme not utilized in binding the substrate HMG CoA, resulting in enhanced potency relative to compounds where Z=H.

In preferred embodiments, the compounds of the invention have the formula I

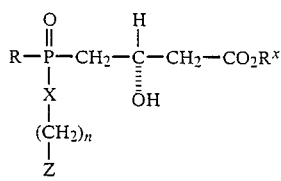  I including salts thereof, wherein R is OH, lower alkoxy or lower alkyl;
R$^x$ is H or lower alkyl;
X is —O— or —NH—;
n is 1 or 2;
Z is a hydrophobic anchor;
and including pharmaceutically acceptable salts thereof.

The terms "salt" and "salts" refer to basic salts formed with inorganic and organic bases. Such salts include ammonium salts, alkali metal salts like, lithium, sodium and potassium salts (which are preferred), alkaline earth metal salts like the calcium and magnesium salts, salts with organic bases, such as amine like salts, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

Examples of hydrophobic anchors which may be included in accordance with the present invention include, but are not limited to

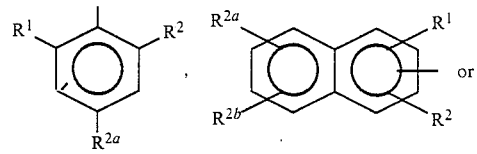

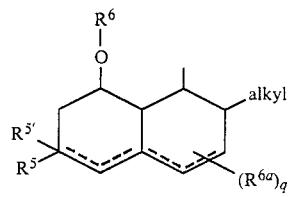

wherein the dotted lines represent optional double bonds, for example,

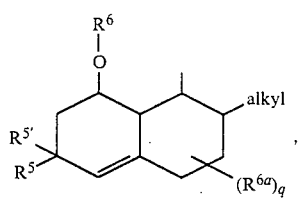

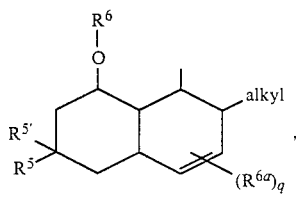

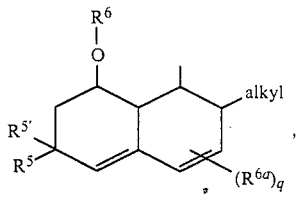

-continued

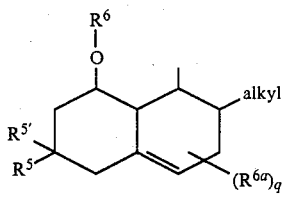

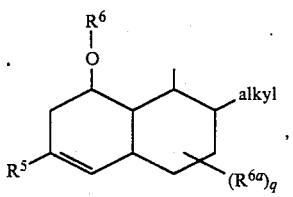

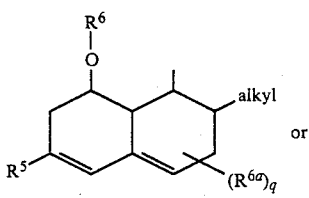

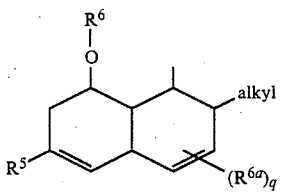

wherein $R^1$, $R^2$, $R^{2a}$ and $R^{2b}$ may be the same or different and are each independently selected from H, halogen, lower alkyl, haloalkyl, phenyl, substituted phenyl or $OR^Y$ wherein $R^Y$ is H, alkanoyl, benzoyl, phenyl, halophenyl, phenyl-lower alkyl, lower alkyl, cinnamyl, haloalkyl, allyl, cycloalkyl-lower alkyl, adamantyl-lower alkyl or substituted phenyl-lower alkyl.

Where Z is

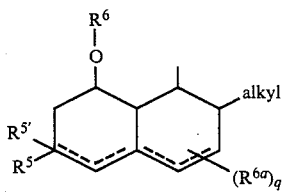

$R^5$ and $R^{5'}$ are the same or different and are H, lower alkyl or OH;
$R^6$ is lower

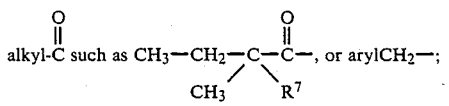

$R^{6a}$ is lower alkyl, hydroxy, oxo or halogen; q is 0, 1, 2 or 3, and
$R^7$ is H or lower alkyl;
Thus, the compounds of formula I encompass

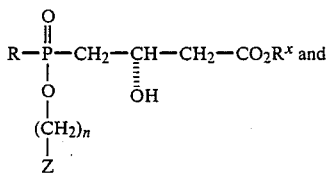

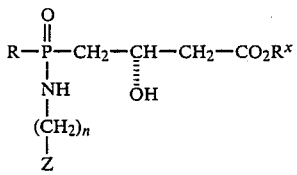

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkylaryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens (Cl, Br of F), 1, 2 or 3 lower alkoxy groups, 1, 2 or 3 hydroxy groups, 1, 2 or 3 phenyl groups, 1, 2 or 3 alkanoyloxy group, 1, 2 or 3 benzoyloxy groups, 1, 2 or 3 haloalkyl groups, 1, 2 or 3 halophenyl groups, 1, 2 or 3 allyl groups, 1, 2 or 3 cycloalkylalkyl groups, 1, 2 or 3 adamantylalkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, 1, 2 or 3 thiol groups, and/or 1, 2 or 3 alkylthio groups with the aryl group preferably containing 3 substituents.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "halogen" or "halo" as used herein refers to chlorine, bromine, fluorine, iodine and $CF_3$, with chlorine or fluorine being preferred.

Preferred are those compounds of formula I which have the following structure

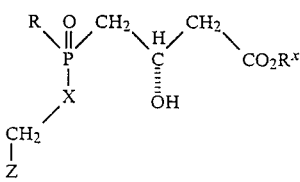

II wherein
R is OH, OLi; $R^x$ is Li or H;
X is O or NH; and
Z is

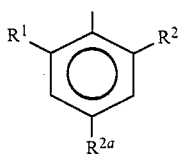

wherein $R^1$ is phenyl which includes an alkyl and-/or halo substitutent
or $R^1$ is benzyloxy which includes a halo substituent;
$R^2$ and $R^{2a}$ are the same and are halogen or lower alkyl;
Z may also preferably be

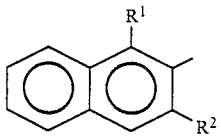

wherein $R^1$ and $R^2$ are as defined immediately above with respect to the compound of formula II, or
Z is

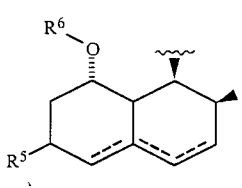

wherein $R^5$ is H, $CH_3$ or OH and $R^6$ is

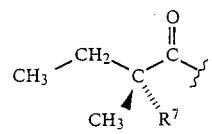

or (substituted)phenylmethyl wherein $R^7$ is H or $CH_3$.

The compounds of formula I of the invention may be prepared according to the following reaction sequence and description thereof.

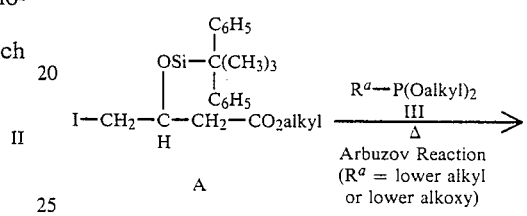

A
Arbuzov Reaction
($R^a$ = lower alkyl or lower alkoxy)

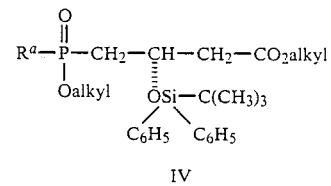

IV

1. $(CH_3)_3$—SiBr, $CH_2Cl_2$
2. $H_2O$

IV $\xrightarrow{\text{Phosphorus ester cleavage}}$

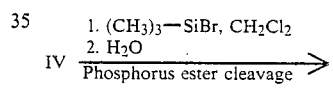

VA. - $R^{a'}$ = lower alkyl where $R^a$ was lower alkyl
VB. - $R^{a'}$ = OH where $R^a$ was lower alkoxy VB
($R^{a'}$ = OH) $\xrightarrow[\text{Pyridine}]{R^bOH—DCC \atop (R^b = \text{lower alkyl})}$ (Esterification)

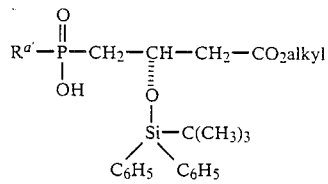

VI

VI or VA. $\xrightarrow[\text{CH}_2\text{Cl}_2 \text{ (Acid Cl Formation)}]{\begin{array}{l}(1) (COCl)_2 \\ (2) Z—(CH_2)_n—XH \text{ (coupling reaction)} \\ (C_2H_5)_3N, \text{DMAP}\end{array}}$

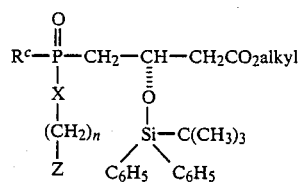

VII ($R^c$ = lower alkyl or lower alkoxy)

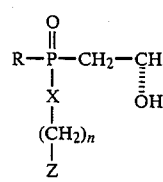

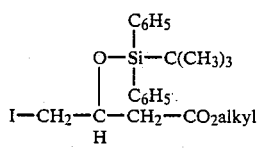

I.

As seen in the above reaction sequence, compounds of Formula I may be prepared by subjecting iodide A to an Arbuzov reaction by heating iodide A

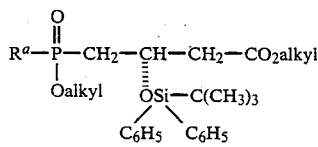

and phosphonite/phosphite III $R^a$—P(Oalkyl)$_2$      III wherein $R^a$ is lower alkyl or lower alkoxy, employing standard Arbuzov conditions and procedures to form phosphinate/phosphonate IV

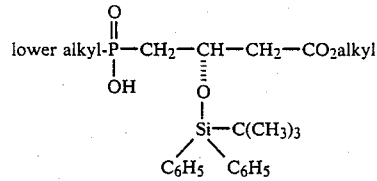

Phosphinate/phosphonate IV is a novel compound and as such is a part of the present invention.

Phosphinate/phosphonate IV is then subjected to a phosphorus ester cleavage by treating a solution of compound IV in an inert organic solvent, such as methylene chloride, sequentially with bis(trimethylsilyl)trifluoroacetamide (BSTFA) and trimethylsilyl bromide, under an inert atmosphere such as argon to form the phosphinic acid VA where $R^a$ in IV is lower alkyl, that is,

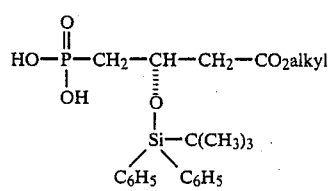

or phosphonic acid VB (wherein $R^a$ in IV is lower alkoxy), that is

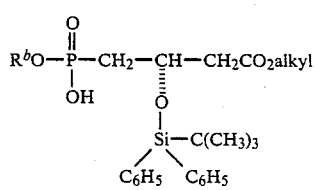

Compounds VA and VB are novel intermediates and as such as part of the present invention.

Where phosphonic acid VB is obtained, it is esterified by treating VB in dry pyridine with alcohol $R^b$OH      VC where $R^b$ is lower alkyl)
and dicyclohexyl carbodiimide and the resulting reaction mixture is stirred under an inert atmosphere, such as argon, to form phosphonic mono alkyl ester VI

[Structure VI:
$R^b$O—P(=O)(OH)—CH$_2$—CH(OSi(C(CH$_3$)$_3$)(C$_6$H$_5$)$_2$)—CH$_2$CO$_2$alkyl]

Ester VI or phosphinic acid VA is then dissolved in an inert organic solvent, such as, methylene chloride, benzene or tetrahydrofuran (THF) and treated with trimethylsilyldiethylamine and stirred under an inert atmosphere such as argon; the mixture is evaporated and then dissolved in methylene chloride (or other appropriate inert organic solvent). The resulting solution is cooled to a temperature within the range of from about 0° C. to about 25° C., treated with oxalyl chloride and then evaporated to give crude phosphonochloridate. The phosphonochloridate is dissolved in inert organic solvent such as methylene chloride, benzene, pyridine or THF; the solution is cooled to a temperature within the range of from about −20° C. to about 0° C. and treated with Z—(CH$_2$)$_n$—XH      B employing a molar ratio of VI or VA:B of within the range of from about 0.5:1 to about 3:1 and preferably from about 1:1 to about 2:1, followed by triethylamine and catalytic 4-dimethylaminopyridine (DMAP) to form adduct VII

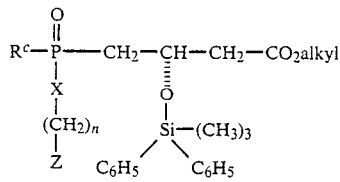
VII wherein R$^c$ is lower alkyl or lower alkoxy.

Compound VII is subjected to silyl ether cleavage by treating a VII in an inert organic solvent such as tetrahydrofuran, with glacial acetic acid and tetrabutylammonium fluoride to form ester VIII

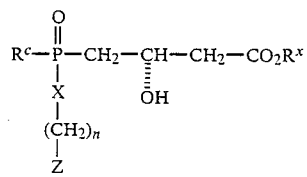
VIII (R$^x$ = alkyl)

The ester VIII may then be hydrolyzed to the corresponding alkali metal salt or acid, that is, where R$^x$ is alkali metal or H by treatment with strong base such as lithium hydroxide in the presence of dioxane, tetrahydrofuran or other inert organic solvent, under an inert atmosphere such as argon, at 25° C., employing a molar ratio of base:ester VIII of within the range of from about 1:1 to about 1.1:1 for form the corresponding alkali metal salt

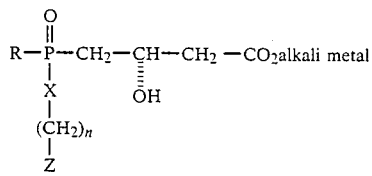
VIIIA wherein R is lower alkyl or lower alkoxy.

Compound VIIIA may then be treated with strong acid such as HCl to form the corresponding acid VIIIB

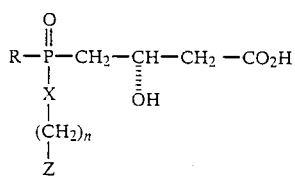
VIIIB

The ester VIII where R is lower alkoxy may be converted to the corresponding di-alkali metal salt by treating ester VIII with strong base at 50°–60° C. employing a molar ratio of base:ester VIII of within the range of from about 2:1 to about 4:1 to form VIIIC

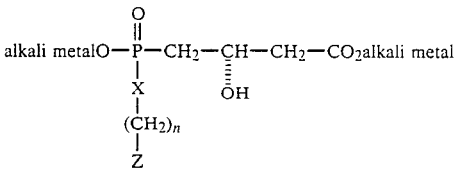
VIIIC

The di-alkali metal salt VIIIC may be converted to the corresponding acid wherein R is OH by treatment with strong acid such as HCl to form VIIID

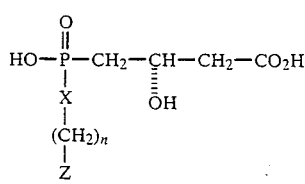
VIIID

The iodide starting material A may be prepared starting with the bromide C

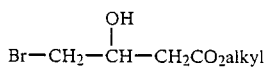
C (prepared employing procedures as described in Tetrahedron Lett. 26, 2951 (1985))

which is dissolved in solution in dimethylformamide (DMF) with imidazole and 4-dimethylamino pyridine and the resulting solution is treated with t-butyldiphenyl silyl chloride under an inert atmosphere such as argon to form the silyl ether D

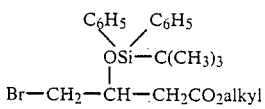
D

A solution of silyl ether D in an inert organic solvent such as methyl ethyl ketone or DMF is treated with sodium iodide under an inert atmosphere such as argon, to form iodide A.

The starting compound B

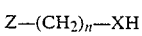
B may be prepared as described below depending upon the definition of Z and X.

Thus, compounds of formula B wherein Z is

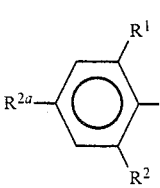

and X is O, that is, compounds of the structure

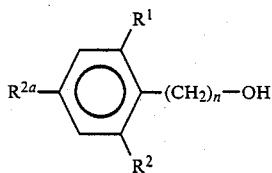      B1 may be prepared by treating aldehyde E

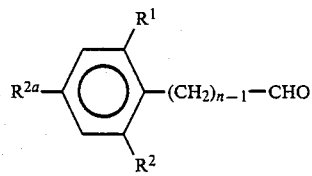      E with a reducing agent such as lithium aluminum hydride or sodium borohydride.

Compounds of formula B where Z is

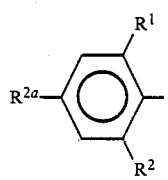

And X is N, that is compounds of the structure

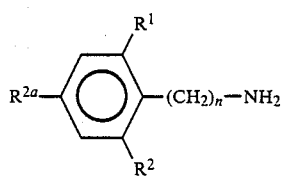      B2 may be prepared by oxidizing the aldehyde E by treating E in solution with acetone with, for example, Jones reagent to form the acid F

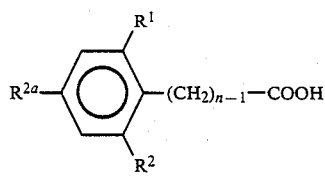      F which in suspension with methylene chloride is treated with oxalyl chloride to form the corresponding acid chloride which is dissolved in an inert organic solvent such as tetrahydrofuran, and treated with a mixture of concentrated ammonium hydroxide in tetrahydrofuran to form an amide of the structure

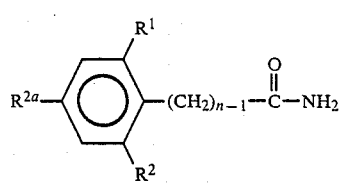      G

Amide G is then reduced to the corresponding amide B² by treating G with a reducing agent such as lithium aluminum hydride.

Starting compounds of formula B wherein Z is

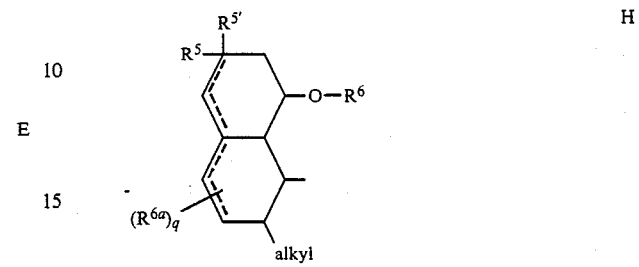      H and X is O or —NH—, that is, compounds of the structure

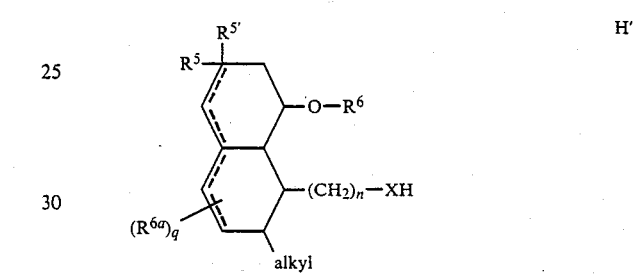      H' where X is O are disclosed by C. H. Heathcock et al, J. Org. Chem. 50, 1190 (1985). Compounds of formula H' were X is NH may be prepared by the reductive amination of

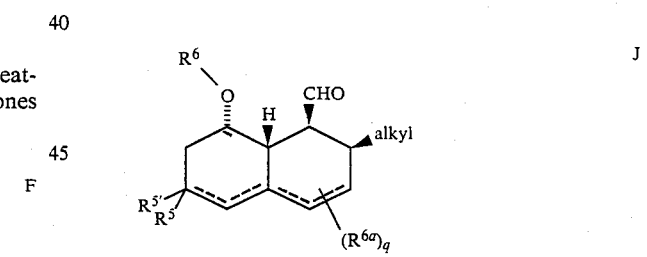      J (prepared as disclosed by C. H. Heathcock et al, supra)

by treating J with ammonium acetate and sodium cyanoborohydride in the presence of an alcohol solvent such as methanol.

Starting compound of formula B wherein Z is

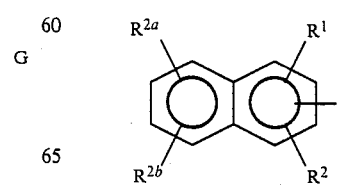

and X is O, that is, compounds of the structure

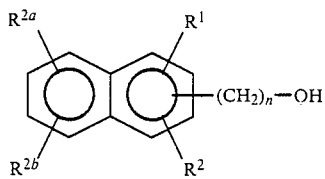  M are disclosed in WO 8402-903-A and GB 2,162,179A both filed in the name of Sandoz.

Starting compounds of formula B wherein Z is

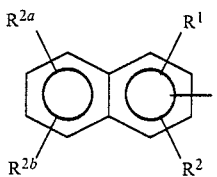

and X is NH, that is, compounds of the structure

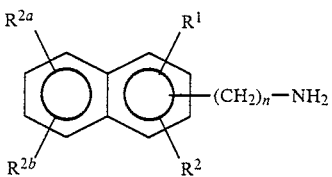  N may be prepared by the reductive amination of the aldehyde O

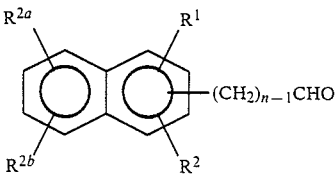  O by treating O with ammonium acetate and sodium cyanoborohydride in the presence of an alcohol solvent such as methanol.

The compounds of the invention may be prepared as racemic mixtures and may later be resolved to obtain the S-isomer which is preferred. However, the compounds of the invention may be prepared directly in the form of their S-isomers as described herein and in the working examples set out hereinafter.

The compounds of the invention are inhibitors of 3-hydroxy-3-methyl-glutaryl coenzyme A (HMG-CoA) reductase and thus are useful in inhibiting cholesterol biosynthesis as demonstrated by the following tests.

(1) Rat Hepatic HMG-CoA Reductase

Rat hepatic HMG-CoA reductase activity is measured using a modification of the method described by Edwards (Edwards, P.A., et al., J. Lipid Res. 20:40, 1979). Rat hepatic microsomes are used as a source of enzyme, and the enzyme activity is determined by measuring the conversion of the $^{14}$C-HMG-CoA substrate to $^{14}$C-mevalonic acid.

a. Preparation of Microsomes

Livers are removed from 2-4 cholestyramine-fed, decapitated, Sprague Dawley rats, and homogenized in phosphate buffer A (potassium phosphate, 0.04M, pH 7.2; KCl, 0.05M; sucrose, 0.1M; EDTA, 0.03M; aprotinin, 500 KI units/ml). The homogenate is spun at 16,000×g for 15 minutes at 4° C. The supernatant is removed and recentrifuged under the same conditions a second time. The second 16,000×g supernatant is spun at 100,000×g for 70 minutes at 4° C. Pelleted microsomes are resuspended in a minimum volume of buffer A (3-5 ml per liver), and homogenized in a glass/glass homogenizer. Dithiothreitol is added (10 mM), and the preparation is aliquoted, quick frozen in acetone/dry ice, and stored at −80° C. The specific activity of the first microsomal preparation was 0.68 nmole mevalonic acid/mg protein/minute.

b. Enzyme Assay

The reductase is assayed in 0.25 ml which contains the following components at the indicated final concentrations:

| | |
|---|---|
| 0.04 M | Potassium phosphate, pH 7.0 |
| 0.05 M | KCl |
| 0.10 M | Sucrose |
| 0.03 M | EDTA |
| 0.01 M | Dithiothreitol |
| 3.5 mM | NaCl |
| 1% | Dimethylsulfoxide |
| 50-200 μg | Microsomal protein |
| 100 μM | $^{14}$C—[DL]HMG-CoA (0.05 μCi, 30-60 mCi/mmole) |
| 2.7 mM | NADPH (nicotinamide adenine dinucleotide phosphate) |

Reaction mixtures are incubated at 37° C. Under conditions described, enzyme activity increases linearly up to 300 μg microsomal protein per reaction mixture, and is linear with respect to incubation time up to 30 minutes. The standard incubation time chosen for drug studies is 20 minutes, which results in 12-15% conversion of HMG-CoA substrate to the mevalonic acid product. [DL-]HMG-CoA substrate is used at 100 μM, twice the concentration needed to saturate the enzyme under the conditions described. NADPH is used in excess at a level 2.7 times the concentration required to achieve maximum enzyme velocity.

Standardized assays for the evaluation of inhibitors are conducted according to the following procedure. Microsomal enzyme is incubated in the presence of NADPH at 37° C. for 15 minutes. DMSO vehicle with or without test compound is added, and the mixture further incubated for 15 minutes at 37° C. The enzyme assay is initiated by adding $^{14}$C-HMG-CoA substrate. After 20 minutes incubation at 37° C. the reaction is stopped by the addition of 25 μl of 33% KOH. $^3$H-mevalonic acid (0.05 μCi) is added, and the reaction mixture allowed to stand at room temperature for 30 minutes. Fifty μl 5N HCl is added to lactonize the mevalonic acid. Bromophenol blue is added as a pH indicator to monitor an adequate drop in pH. Lactonization is allowed to proceed for 30 minutes at room temperature. Reaction mixtures are centrifuged for 15 minutes at 2800 rpm. The supernatants are layered onto 2 grams AG 1-X8 anion exchange resin (Biorad, formate form) poured in 0.7 cm (id) glass columns, and eluted with 2.0 ml H$_2$O. The first 0.5 ml is discarded, and the next 1.5 ml is collected and counted for both tritium and carbon 14 in 10.0 ml Opti-fluor scintillation fluid. Results are calculated as nmoles mevalonic acid produced per 20 minutes, and are corrected to 100% recovery of tritium. Drug effects are expressed as I$_{50}$ values (concentration of drug producing 50% inhibition of enzyme activity)

derived from composite dose response data with the 95% confidence interval indicated.

Conversion of drugs in lactone form to their sodium salts is accomplished by solubilizing the lactone in DMSO, adding a 10-fold molar excess of NaOH, and allowing the mixture to stand at room temperature for 15 minutes. The mixture is then partially neutralized (pH 7.5-8.0) using 1N HCl, and diluted into the enzyme reaction mixture.

(2) Cholesterol Synthesis in Freshly Isolated Rat Hepatocytes

Compounds which demonstrate activity as inhibitors of HMG-CoA reductase are evaluated for their ability to inhibit $^{14}$C-acetate incorporation into cholesterol in freshly isolated rat hepatocyte suspensions using methods originally described by Capuzzi et al. (Capuzzi, D.M. and Margolis, S., Lipids, 6:602, 1971).

a. Isolation of Rat Hepatocytes

Sprague Dawley rats (180-220 grams) are anesthetized with Nembutol (50 mg/kg). The abdomen is opened and the first branch of the portal vein is tied closed. Heparin (100-200 units) is injected directly into the abdominal vena cava. A single closing suture is placed on the distal section of the portal vein, and the portal vein is canulated between the suture and the first branching vein. The liver is perfused at a rate of 20 ml/minute with prewarmed (37° C.), oxygenated buffer A (HBSS without calcium or magnesium containing 0.5 mM EDTA) after severing the vena cava to allow drainage of the effluent. The liver is additionally perfused with 200 ml of prewarmed buffer B (HBSS containing 0.05% bacterial collagenase). Following perfusion with buffer B, the liver is excised and decapsulated in 60 ml Waymouth's medium allowing free cells to disperse into the medium. Hepatocytes are isolated by low speed centrifugation for 3 minutes at 50 xg at room temperature. Pelleted hepatocytes are washed once in Waymouth's medium, counted and assayed for viability by trypan blue exclusion. These hepatocyte enriched cell suspensions routinely show 70-90% viability.

b. $^{14}$C-Acetate Incorporation into Cholesterol

Hepatocytes are resuspended at $5 \times 10^6$ cells per 2.0 ml in incubation medium (IM) [0.02M Tris-HCl (pH 7.4), 0.1M KCl, 3.3 mM sodium citrate, 6.7 mM nicotinamide, 0.23 mM NADP, 1.7 mM glucose-6-phosphate].

Test compounds are routinely dissolved in DMSO or DMSO:H$_2$O (1:3) and added to the IM. Final DMSO concentration in the IM is ≦1.0%, and has no significant effect on cholesterol synthesis.

Incubation is initiated by adding $^{14}$C-acetate (58 mCi/mmol, 2 μCi/ml), and placing the cell suspensions (2.0 ml) in 35 mm tissue culture dishes, at 37° C. for 2.0 hours. Following incubation, cell suspensions are transferred to glass centrifuge tubes and spun at 50 xg for 3 minutes at room temperature. Cell pellets are resuspended and lysed in 1.0 ml H$_2$O, and placed in and ice bath.

Lipids are extracted essentially as described by Bligh, E. G. and W. J. Dyer, Can. J. Biochem. and Physiol., 37:911, 1959. The lower organic phase is removed and dried under a stream of nitrogen, and the residue resuspended in (100 μl) chloroform:methanol (2:1). The total sample is spotted on silica gel (LK6D) thin-layer plates and developed in hexane:ethyl ether:acetic acid (75:25:1). Plates are scanned and counted using a BioScan automated scanning system. Radiolabel in the cholesterol peak (RF 0.28) is determined and expressed at total counts per peak and as a percent of the label in the total lipid extract. Cholesterol peaks in control cultures routinely contain 800-1000 cpm, and are 9-20% of the label present in the total lipid extract; results compatable with Capuzzi, et al., indicating 9% of extracted label in cholesterol.

Drug effects (% inhibition of cholesterol synthesis) are determined by comparing % of label in cholesterol for control and drug treated cultures. Dose response curves are constructed from composite data from two or more studies, and results are expressed as $I_{50}$ values with a 95% confidence interval.

(3) Cholesterol Synthesis in Human Skin Fibroblasts

Compound selectivity favoring greater inhibitory activity in hepatic tissue would be an attribute for a cholesterol synthesis inhibitor. Therefore, in addition to evaluating cholesterol synthesis inhibitors in hepatocytes, these compounds are also tested for their activity as inhibitors of cholesterol synthesis in cultured fibroblasts.

a. Human Skin Fibroblast Cultures

Human skin fibroblasts (passage 7-27) are grown in Eagles' minimal essential medium (EM) containing 10% fetal calf serum. For each experiment, stock cultures are trypsonized to disperse the cell monolayer, counted, and plated in 35 mm tissue culture wells ($5 \times 10^5$ cells/2.0 ml). Cultures are incubated for 18 hours at 37° C. in 5% CO$_2$/95% humidified room air. Cholesterol biosynthetic enzymes are induced by removing the serum containing medium, washing the cell monolayers, and adding 1.0 ml of EM containing 1.0% fatty acid free bovine serum albumin, and incubating the cultures an additional 24 hours.

b. $^{14}$C-Acetate Incorporation into Cholesterol

Induced fibroblast cultures are washed with EMEM$_{100}$ (Earle's minimal essential medium). Test compounds are dissolved in DMSO or DMSO:EM (1:3) (final DMSO concentration in cell cultures ≦1.0%), added to the cultures, and the cultures preincubated for 30 minutes at 37° C. in 5% CO$_2$/95% humidified room air. Following preincubation with drugs, [1-$^{14}$C]Na acetate (2.0 μCi/ml, 58 mCi/mmole) is added, and the cultures reincubated for 4 hours. After incubation, the culture medium is removed, and the cell monolayer (200 μg cell protein per culture) is scraped into 1.0 ml of H$_2$O. Lipids in the lysed cell suspension are extracted into chloroform:methanol as described for hepatocyte suspensions. The organic phase is dried under nitrogen, and the residue resuspended in chloroform:methanol (2:1) (100 μl), and the total sample spotted on silica gel (LK6D) thin-layer plates, and analyzed as described for hepatocytes.

Inhibition of cholesterol synthesis is determined by comparing the percent of label in the cholesterol peak from control and drug-treated cultures. Results are expressed as $I_{50}$ values, and are derived from composite dose response curves from two or more experiments. A 95% confidence interval for the $I_{50}$ value is also calculated from the composite dose response curves.

A further aspect of the present invention is a pharmaceutical composition consisting of at least one of the compounds of formula I in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations, such dosage forms containing from 1 to 2000 mg of active compound per dosage, for use in the treatment. The dose to be administered depends on the unitary dose, the symptoms, and the age and the body weight of the patient.

The compounds of formula I may be administered in a similar manner as known compounds suggested for use in inhibiting cholesterol biosynthesis, such as lovastatin, in mammalian species such as humans, dogs, cats and the like. Thus, the compounds of the invention may be administered in an amount from about 4 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The following working Examples represent preferred embodiments of the present invention. Unless otherwise indicated, all temperatures are expressed in degrees Centigrade. Flash chromatography was performed on either Merck 60 or Whatmann LPS-I silica gel. Reverse phase chromatography was performed on CHP-20 MCI gel resin supplied by Mitsubishi, Ltd.

EXAMPLE 1

(S)-4-[[[4'-Fluoro-3,3',5-trimethyl[1,1'-biphenyl]-2-yl]methoxy]methoxyphosphinyl]-3-hydroxy-butanoic acid, monolithium salt A. N-(2,4-Dimethylbenzylidene)benzeneamine Ref. Merck U.S. Pat. No. 4,375,475, pg. 39.

A solution of freshly distilled 2,4-dimethylbenzaldehyde (Aldrich, 6.97 ml, 50 mmole) and distilled aniline (Aldrich, 4.56 ml, 50 mmole) in dry toluene (80.0 ml) was refluxed for 3.0 hours under argon in a flask equipped with a Dean-Stark apparatus. The mixture was cooled, then evaporated in vacuo to a yellow oil. The crude oil was purified by Kugelrohr distillation (0.5 mm Hg, 160°–180° C.) to give 8.172 g (78.1%) of desired title benzeneimine as a light yellow oil which crystallized on standing to a low melting solid. TLC (4:1) Hex-acetone, RF=0.67 and 0.77 (geometric isomers), U.V. and $I_2$.

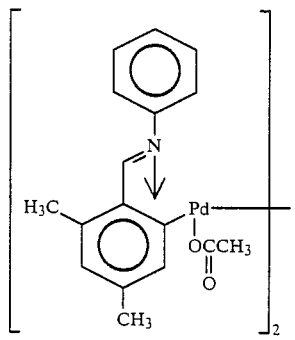

Ref. Merck U.S. Pat. No. 4,375,475, pg. 39.

A mixture of Part A benzeneimine (6.0 g, 28.7 mmol) in glacial HOAc (144 ml) was treated with palladium (II) acetate (6.44 g, 28.7 mmole) and the clear, red homogeneous solution refluxed under argon for one hour. The resulting turbid mixture was filtered warm through a packed ½" bed of Celite into 900 ml of $H_2O$. Precipitated orange solid was collected by filtration and dried in vacuo at 65° C. over $P_2O_5$ for 16.0 hours to give 10.627 g (85.5%) of desired title palladium complex as an orange solid with m.p.=194°–196° C. (Literature m.p. of a recrystallized analytical sample=203°–205° C.).

C. 4'-Fluoro-3,3',5-trimethyl[1,1'-biphenyl]-2-carboxaldehyde (1) Bromo[4-fluoro-3-methylphenyl]-magnesium Ref. Merck U.S. Pat. No. 4,375,475, pp. 37 and 38.

The title Part C(1) Grignard reagent was prepared by adding 5-bromo-2-fluorotoluene (22.5 g, 60.9 mmole, Fairfield Chemical Co.) dropwise at a rate sufficient to maintain the reaction at reflux to stirred magnesium turnings (1.35 g, 55.4 mmole, 8.0 eq.) in dry $Et_2O$ (70.0 ml). The reaction was initiated in an ultrasound device. After bromide addition was complete, the mixture was stirred for one hour under argon at room temperature, refluxed for 15 minutes and then allowed to cool to room temperature.

(2) 4'-Fluoro-3,3',5-trimethyl[1,1'-biphenyl]-2-carboxaldehyde

In a second flask, a mixture of the Part B dipalladium complex (3.0 g, 6.92 mmole) and triphenylphosphine (14.52 g, 55.4 mmole, 8.0 eq.) in dry benzene (100 ml) was stirred at room temperature under argon for 30 minutes. Freshly prepared and filtered (glass wool plug) Part C (1) Grignard reagent was then added in one portion by means of a cannula to this solution and the mixture was stirred for 1.5 hours at room temperature under argon. 6.0N HCl (35 ml) was added, the mixture stirred an additional hour at room temperature, then filtered through packed Celite (½" bed). The filtrate was extracted with $Et_2O$ (250 ml), the extract washed with brine (2×100 ml), dried over anhydrous $MgSO_4$ and evaporated in vacuo to give 13.35 g of a viscous orange oil which crystallized on standing. The crude orange solid was purified by flash chromatography on silica gel (700 g) eluting with hexane, followed by (95:5) hexane-$Et_2O$. Product fractions were evaporated to give 1.507 g (89.9%) of desired title aldehyde as a light yellow solid with m.p.=72°–75° C.) (Literature reports m.p.=73°–74° C.). TLC: (95:5) Hex-$Et_2O$, Rf=0.40, U.V. and PMA.

D. 4'-Fluoro-3,3',5-trimethyl[1,1'-biphenyl]-2-methanol

A cooled (0° C., ice bath) solution of dry $Et_2O$ (15.0 ml) was treated with $LiAlH_4$ (259 mg, 6.82 mmole, 0.55 eq.) and the gray suspension treated dropwise over 15 minutes with a solution of the Part C aldehyde (3.0 g, 12.4 mmole) in dry $Et_2O$ (15 ml). The mixture was stirred at room temperature under argon for 30 minutes, then cooled back to 0° C. and quenched by sequential dropwise addition of 260 μl $H_2O$, 260 μl of 15% NaOH and 780 μl $H_2O$. The suspension was diluted with EtOAc, filtered through anhydrous $Na_2SO_4$ over packed Celite (¼" bed) and the colorless filtrate evaporated in vacuo to give 2.99 g (98.8%) of a white solid. Trituration of the crude solid with cold hexane and drying in vacuo afforded 2.467 g (81.6%) of desired title alcohol as a white solid with m.p. 102°–103° C. The TLC: (9:1) Hex-EtOAc, RF=0.24, U.V. and PMA.

E. (S)-3-[[(1,1-Dimethylethyl)diphenylsilyl]oxy]-4-(hydroxymethoxyphosphinyl)-butanoic acid, methyl ester (1) (S)-4-Bromo-3-hydroxybutanoic acid, methyl ester (1)(a) [R-(R*,R*)]-2,3,4-trihydroxybutanoic acid, calcium salt, hydrate Ref. Carbohydrate Research 72, pp. 301–304 (1979).

Calcium carbonate (50 g) was added to a solution of D-isoascorbic acid (44.0 g, 250 mmol) in H$_2$O (625 ml), the suspension cooled to 0° C. (ice bath) and treated portionwise with 30% H$_2$O$_2$ (100 ml). The mixture was stirred at 30°-40° C. (oil bath) for 30 minutes. Darco (10 g) was added and the black suspension heated on a steam bath until evolution of O$_2$ ceased. The suspension was filtered through Celite, evaporated in vacuo (bath temperature 40° C.). The residue was taken up in H$_2$O (50 ml), warmed on a steam bath and CH$_3$OH was added until the solution was turbid. The gummy precipitated solid was collected by filtration and air dried to give 30.836 g (75.2%) of desired calcium salt as a powdery white solid.

TLC (7:2:1) iPrOH—NH$_4$OH—H$_2$O, Rf=0.19, PMA.

(1)(b) [S-(R*,S*)]-2,4-Dibromo-3-hydroxybutanoic acid, methyl ester

Ref. Bock, K. et al., Acta Scandinavica (B) 37, pp. 341-344 (1983).

Part (1)(a) calcium salt (30 g) was dissolved in 30-32% HBr in acetic acid (210 ml) and stirred at room temperature for 24 hours. Methanol (990 ml) was then added to the brown solution and it was stirred overnight. The mixture was evaporated to an orange oil, taken up in CH$_3$OH (75 ml), refluxed for 2.0 hours and evaporated. The residue was partitioned between EtOAc (100 ml) and H$_2$O, the organic phase washed with H$_2$O (2×) and brine then dried over anhydrous Na$_2$SO$_4$ and evaporated to give 22.83 g (90.5%) of crude dibromide as a light orange oil. TLC (1:1) EtOAc-Hex, Rf=0.69, UV & PMA.

(1)(c) (S)-4-Bromo-3-hydroxybutanoic acid, methyl ester

Ref. the same as for preparation of (1)(b).

An argon purged solution of the dibromide (20.80 g, 75.4 mmol) and anhydrous NaOAc (21.0 g) in EtOAc (370 ml) and glacial HOAc (37 ml) was treated with 5% Pd/C (1.30 g) and the black suspension stirred under of H$_2$ (1 atm) while monitoring H$_2$ uptake. After 2.0 hours H$_2$ uptake was complete, the mixture was filtered through Celite, the filtrate washed with saturated NaHCO$_3$ and brine then dried over anhydrous MgSO$_4$ and evaporated to give crude dibromoester as a brown oil. The crude oil was combined with another batch (starting from 36.77 g of the dibromide) and vacuum distilled to give 25.77 g (61.3%) of desired title bromoester as a clear oil with b.p.=79°-80° C. (1.0 mm Hg).

TLC (1:1) EtOAc-Hex, Rf=0.44, PMA.

Anal Calcd for C$_5$H$_9$O$_3$Br: C, 30.48; H, 4.60; Br, 40.56. Found: C, 29.76; H, 4.50; Br, 39.86.

(2) (S)-4-Bromo-3-[[(1,1-dimethylethyl)-diphenylsilyl]oxy]butanoic acid, methyl ester A solution of part E(1) bromohydrin (4.0 g, 20.4 mmol), imidazole (6.94 g, 5.0 eq.), and 4-dimethylamino pyridine (4-DMAP) (12 mg 0.005 eq.) in dry DMF (40 ml) was treated with t-butyldiphenylsilyl chloride (5.84 ml, 1,1 eq.) and the homogeneous mixture stirred overnight under argon at room temperature. The mixture was partitioned between 5% KHSO$_4$ and EtOAc, the organic phase washed with H$_2$O and brine, dried over anhydrous Na$_2$SO$_4$ and evaporated to give 9.32 g (100%) of crude silyl ether as a clear, viscous oil. TLC (3:1) Hex-EtOAc, Rf silyl ether=0.75, U.V. and PMA.

(3) (S)-4-Iodo-3-[[(1,1-dimethylethyl)diphenylsilyl]oxy]butanoic acid, methyl ester A solution of the crude Part E(2) bromide (9.32 g, 201 mmole) in methyl ethyl ketone (60 ml, dried over 4Å sieves) was treated with sodium iodide (15.06 g, 100.5 mmole, 5.0 eq.) and the yellow suspension refluxed for 5.0 hours under argon. The mixture was cooled, diluted with EtOAc, filtered, the filtrate washed with dilute NaHSO$_3$ (until colorless) and brine then dried over anhydrous Na$_2$SO$_4$ and evaporated in vacuo to give 10.17 g of a yellow oil. The crude oil was purified by flash chromatography on silica gel (600 g) eluting with (3:1) Hexane-CH$_2$Cl$_2$. Product fractions were combined and evaporated to give 7.691 g (74.2%, overall yield for both steps) of desired title iodide as a clear, colorless, viscous oil TLC (3:1) Hex-EtOAc, product. Rf=0.75, U.V. and PMA. (Note: product iodide co-spots with starting bromide).

(4) (S)-4-(Diethoxyphosphinyl)-3-[[(1,1-dimethylethyl)diphenylsilyl]oxy]butanoic acid, methyl ester A solution of the iodide (7.691 g) in triethyl phosphite (20 ml) was heated at 155° C. (oil bath) for 3.5 hours under argon. The mixture was cooled and excess phosphite distilled off in vacuo (0.5 mm Hg, 75° C.) to leave a yellow oil (∼8.0 g). The crude oil was purified by flash chromatography on silica gel (400 g) eluting with (4:1) Hexane-acetone. Product fractions were evaporated to give 3.222 g (41.1%) of desired title phosphonate as a clear, colorless, viscous oil. TLC (1:1) Hex-acetone, Rf=0.51, U.V. and PMA. Additionally 2.519 g (61.1% corrected yield) of starting Part (3) iodide was recovered.

(5) (S)-3-[[(1,1-Dimethylethyl)diphenylsilyl]oxy]-4-phosphonobutanoic acid, methyl ester A solution of the Part (4) phosphonate (9.85 g, 20.0 mmole) in dry CH$_2$Cl$_2$ (60 ml) was treated sequentially with bistrimethylsilyltrifluoroacetamide (BSTFA) (5.31 ml, 32.0 mmole, 1.6 eq.) and trimethylsilyl bromide (TMSBr) (6.60 ml 50.0 mmole, 2.5 eq.) and the clear mixture stirred overnight under argon at room temperature. 5% KHSO$_4$ (80 ml) was added and the mixture was extracted with EtOAc. The aqueous phase was saturated with NaCl and re-extracted with EtOAc. The combined organic layers were washed with brine, dried over anhydrous Na$_2$SO$_4$ and evaporated in vacuo to give crude title phosphonic acid as a viscous oil. TLC (7:2:1) iPrOH-NH$_4$OH-H$_2$O, Rf=0.30, U.V. and PMA.

(6) (S)-3-[[(1,1-Dimethylethyl)diphenylsilyl]oxy]-4-(hydroxymethoxyphosphinyl)butanoic acid, methyl ester Part (5) crude phosphonic acid (∼20.0 mmole) in dry pyridine (25 ml) was treated with dried CH$_3$OH (over 3Å sieves, 1.62 ml, 40.0 mmole, 2.0 eq.) and dicyclohexyl carbodiimide (DCC) (4.54 gm, 22.0 mmole, 1.10 eq.) and the resulting white suspension stirred under argon at room temperature overnight. Pyridine was removed in vacuo, then azeotroped with benzene (2×15 ml). The residual oil was dissolved in EtOAc, filtered and washed with 1.0N HCl and brine, dried over anhydrous Na$_2$SO$_4$ and evaporated in vacuo to give 8.272 g of crude title ester as an oil containing a small amount of precipitated dicyclohexyl urea (DCU). TLC (7:2:1) iPrOH—NH$_4$—OH H$_2$O, Rf=0.60, U.V. and PMA.

F. (S)-4-[[[4'-Fluoro-3,3',5-trimethyl[1,1'-biphenyl]-2-yl]methoxyphosphinyl]-3-t-butyldiphenylsilyloxybutanoic acid, methyl ester Part E crude phosphonic acid mono methyl ester (6.595 gm, ∼14.7 mmole) was dissolved in dry CH$_2$Cl$_2$ (30 ml), treated with distilled trimethylsilyldiethylamine (5.60 ml, 29.4 mmole, 2.0 eq.) and stirred under argon at room temperature for 1 hour. The mixture was evaporated in vacuo, chased with benzene (1×30 ml) and dried in vacuo. The light yellow viscous oil was dissolved in dry CH$_2$Cl$_2$ (30 ml) and DMF (dried over 4Å sieves, 2 drops), the clear solution cooled to −10° C. (salt/ice bath) and treated dropwise via syringe with distilled oxalyl chloride (1.41 ml, 16.2 mmole, 1.1 eq.). Vigorous gas evolution was evident and the solution became deeper yellow in color. The mixture was stirred under argon at −10° C. for 15 minutes then allowed to stir at room temperature for 1 hour. The mixture was evaporated in vacuo, chased with benzene (1×30 ml) and dried in vacuo to give crude phosphonochloridate as a yellow oil.

To a solution of the crude phosphonochloridate (~14.7 mmole) in dry CH$_2$Cl$_2$ (10 ml) was added dropwise a solution of the Part D biphenyl alcohol (2.06 g, 8.43 mmole) in dry pyridine (15 ml) and the resulting mixture stirred at room temperature under argon for 16 hours. The mixture was evaporated to dryness and the residue partitioned between 5% KHSO$_4$ and EtOAc. The organic phase washed with saturated NaHCO$_3$ and brine then dried over anhydrous Na$_2$SO$_4$ and evaporated in vacuo to give 8.290 g of a brown oil. The crude product was purified by flash chromatography on silica gel (370 g) eluting with (70:30) Hexane-acetone. Product fractions were combined and evaporated to give 3.681 g (66%) of the desired title phosphonate as a pale yellow oil. TLC (3:2) Hexane-acetone, Rf=0.59, U.V. and PMA.

G. (S)-4-[[[4'-Fluoro-3,3',5-trimethyl[1,1'-biphenyl]-2yl]methoxyphosphinyl]3-hydroxybutanoic acid, methyl ester A mixture of the Part F silyl ether (1.103 g, 1.66 mmole) in dry THF (20.0 ml) was treated with glacial acetic acid (380 μl, 6.64 mmole, 4.0 eq.) and a 1.0M tetrabutylammonium fluoride solution (4.98 ml, 4.98 mmole, 3.0 eq.) and the clear yellow solution stirred overnight at room temperature under argon. The mixture was partitioned between cold H$_2$O and EtOAc, the organic phase washed with saturated NaHCO$_3$ and brine, dried over anhydrous Na$_2$SO$_4$ and evaporated to a viscous yellow oil (1.174 g). The crude oil was purified by flash chromatography on silica gel (47 g) eluting with (85:15) CH$_2$Cl$_2$-Acetone. Product fractions were evaporated to give 679 mg (93.1%) of desired title alcohol as a clear viscous oil. TLC (1:1) Hexane-acetone, Rf=0.41, U.V. and PMA.

H. (S)-4-[[[4'-Fluoro-3,3',5-trimethyl[1,1'-biphenyl]-2-yl]methoxy]methoxyphosphinyl]-3-hydroxy-butanoic acid, monolithium salt A solution of the Part G methyl ester (184 mg, 0.420 mmole) in dioxane (5.0 ml) was treated with 1.0N LiOH (0.50 ml, 1.2 eq.) and the mixture stirred at room temperature under argon for 3 hours. The mixture was diluted with H$_2$O, filtered through a 0.4 μm polycarbonate membrane and evaporated in vacuo. The residue dissolved in H$_2$O (75 ml), frozen and lyophilized. The crude acid was dissolved in a minimum amount of H$_2$O and chromatographed on a 100 ml bed of CHP-20 resin eluting with a H$_2$O/CH$_3$CN linear gradient system. Product fractions were evaporated, dissolved in H$_2$O (50 ml), filtered through 0.4 μm polycarbonate membrane and lyophilized to give 174 mg (89.1% based on weight of hydrate) of desired title mono-lithium salt as a white solid. TLC (7:2:1) iPrOH—NH$_4$OH—H$_2$O, Rf=0.58, U.V. And PMA.

Anal Calcd for C$_{21}$H$_{25}$O$_6$PFLi+1.95 moles H$_2$O (MW 465.46): C, 54.19; H, 6.26; F, 4.08; P. 6.65. Found: C, 54.19; H, 6.21; F, 4.29; P, 6.43.

H$^1$ NMR (400 HMz):

| δ 1.74–2.08 ppm | (2H, m, —PO(OCH$_3$)CH$_2$—) |
|---|---|
| 2.30 | (3H, s, aromatic methyl) |
| 2.32 | (3H, d, aromatic methyl α to fluorine, J$_{HF}$2.2 Hz) |
| 2.35–2.62 | (2H, m, —CH$_2$CO$_2$Li) |
| 2.46 | (3H, s, aromatic methyl) |
| 3.57 & 3.63 | (3H, 2 doublets, —OP(OCH$_3$)—, 2 diastereomers, J$_{H-p}$ = 10.3 Hz) |
| 4.28 | (1H, m, —CH$_2$CH(OH)CH$_2$CO$_2$Li) |
| 4.97 | (2H, m, PhCH$_2$OP(OCH$_3$)R) with O‖ above P |
| 6.87–7.25 | (5H, m, aromatic H's) |

EXAMPLE 2

(S)-4-[[[4'-Fluoro-3,3',5-trimethyl[1,1'-biphenyl]-2-yl]methoxy]hydroxyphosphinyl]-3-hydroxybutanoic acid, dilithium salt A solution of the Example 1 diester (374 mg, 0.853 mmole) in dioxane (8.0 ml) was treated with 1.0N LiOH (2.6 ml, 3.0 eq.) and heated at 50° C. (oil bath) for 5.0 hours under argon. A white precipitate was evident. The mixture was diluted with H$_2$O and filtered. The aqueous solution was extracted once with Et$_2$O, filtered through a 0.4 μm polycarbonate membrane and concentrated in vacuo. The crude product was chromatographed on CHP-20 resin (100 ml bed) eluting with a H$_2$O/CH$_3$CN linear gradient system. Product fractions were evaporated in vacuo, taken up in H$_2$O (50 ml), filtered through a 0.4 μm polycarbonate membrane and lyophilized to give 260 mg (67.1% based on hydrate weight) of desired title di-lithium salt as a white solid. TLC (7:2:1). PrOH—NH$_4$OH—H$_2$O, Rf=0.47, U.V. and PMA.

Anal Calcd for C$_{20}$H$_{22}$O$_6$PFLi$_2$+1.77 moles H$_2$O: C, 52.88, H, 5.67; F, 4.18; P, 6.82. Found: C, 52.88; H, 5.26; F, 4.24; P, 6.43.

H$^1$ NMR (400 MHz, CD$_3$OD):

| δ 1.69 ppm | (2H, m, —OPCH$_2$CH(OH)—) with O‖ above P |
|---|---|
| 2.26–2.42 | (2H, m, CH$_2$CO$_2$Li) |
| 2.30 | (3H, s, aromatic methyl) |
| 2.31 | (3H, d, aromatic methyl α to F, J$_{HF}$ = 1.9 Hz) |
| 2.38 | (3H, s, aromatic methyl) |
| 4.22 | (1H, m, —CH(OH)CH$_2$—) |
| 4.75 | (2H, m, PhCH$_2$OP—) with O‖ above P |
| 6.86–7.23 | (5H, m, aromatic protons) |

EXAMPLE 3

(3S)-4-[[[4'-Fluoro-3,3',5-trimethyl[1,1'-biphenyl]-2-yl]methoxy]methylphosphinyl]-3-hydroxybutanoic acid, monolithium salt A. (S)-4-[(Chloro)methylphosphinyl]-3-[[(1,1-dimethylethyl)diphenylsilyl]oxy]butanoic acid, methyl ester The title phosphinochloridate compound is prepared as described in Example 6 Part B first three paragraphs.

B. (3S)-4-[[[4'-Fluoro-3,3',5-trimethyl[1,1'-biphenyl]-2-yl]methoxy]methylphosphinyl]-3-t-butyldiphenylsilyloxybutanoic acid, methyl ester A cooled (0° C., ice bath) solution of Part A phosphinochloridate (~2.2 mmole) and Example 1 Part C(2) biphenyl alcohol (429 mg, 2.2 mmole, 1.0 eq) in dry $CH_2Cl_2$ (10 ml) was treated with $Et_3N$ (425 μl, 3.04 mmole, 1.4 eq) and 4-DMAP (27 mg, 0.22 mmole) and the orange solution stirred at room temperature overnight under argon. The mixture was partitioned between 5% $KHSO_4$ and EtOAc, the organic layer washed with brine, dried over anhydrous $Na_2SO_4$ and evaporated to give 1.1 g of an orange oil. The crude oil was purified by flash chromatography on LPS-1 silica gel (44 g) eluting with (1:1) EtOAc:Hexane. Product fractions were combined and evaporated to give 298 mg (21%) of desired coupled title product as a pale yellow oil. Also 460 mg (67% corrected yield) of starting Example 1 Part C(2) biphenyl alcohol was recovered. TLC (1:1) EtOAc:Hex, Rf=0.18 UV and PMA.

C. (3S)-4[[[4'-Fluoro-3,3',5-trimethyl[1,1'-biphenyl]-2-yl]methoxy]methylphosphinyl]-3-hydroxybutanoic acid, methyl ester A solution of the Part B silyl ether (298 mg, 0.46 mmole) in dry THF (6.0 ml) was treated with glacial HOAc (110 μl, 1.84 mmole, 4.0 eq) and a 1.0M in THF solution of tetrabutylammonium fluoride (1.43 ml, 3.1 eq) and the resulting solution stirred overnight under argon at room temperature. The mixture was partitioned between cold $H_2O$ and EtOAc, the organic phase washed with saturated $NaHCO_3$ and brine, dried over anhydrous $Na_2SO_4$ and evaporated to a yellow oil (273 mg). The crude oil was purified by flash chromatography on LPS-1 silica gel (11 g) eluting with (3:2) Hex-acetone. Product fractions were combined and evaporated to give 150 mg (80%) of desired title alcohol as a viscous oil. TLC (1:1) Hex:acetone, Rf=0.23, UV and PMA.

D. (3S)-4-[[[4'-Fluoro-3,3',5-trimethyl[1,1'-biphenyl]-2-yl]methoxy]methylphosphinyl]-3-hydroxybutanoic acid, monolithium salt A solution of the Part C methyl ester (150 mg, 0.367 mmole) in dioxane (3.0 ml) was treated with 1.0N LiOH (0.44 ml, 1.2 eq.) and the resulting white suspension was stirred at room temperature under argon for 2 hours. The mixture was diluted with $H_2O$, filtered through a 0.4 μm polycarbonate membrane and evaporated in vacuo to a colorless glass.

The crude product was taken up in a minimum amount of $H_2O$ and chromatographed on HP-20 (100 ml bed) eluting with a $H_2O/CH_3CN$ linear gradient. Product fractions were evaporated, taken up in $H_2O$ (50 ml), filtered through a 0.4 μm polycarbonate membrane and lyophilized to give 130 mg (79% based on hydrate weight) of desired title lithium salt as a white solid. TLC (8:1:1) $CH_2Cl_2$—$CH_3OH$—HOAc, Rf=0.52, UV and PMA.

Anal Calcd for $C_{21}H_{25}O_5FLiP+1.73$ moles $H_2O$ (MW 445.49): C, 56.61; H, 6.44; F. 4.26; P, 6.95. Found: C, 56.67; H, 6.36; F, 4.31; P, 7.43

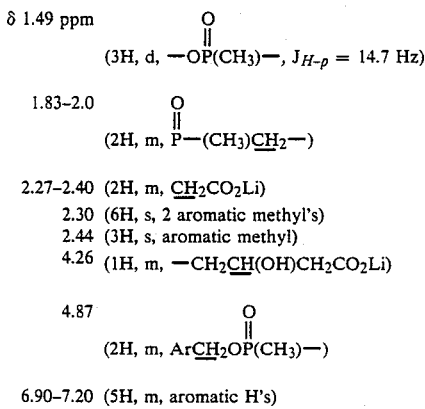

$H^1$ NMR (400 MHz):

δ 1.49 ppm (3H, d, —OP(CH$_3$)—, $J_{H-p}$ = 14.7 Hz)

1.83–2.0 (2H, m, P—(CH$_3$)CH$_2$—)

2.27–2.40 (2H, m, CH$_2$CO$_2$Li)

2.30 (6H, s, 2 aromatic methyl's)

2.44 (3H, s, aromatic methyl)

4.26 (1H, m, —CH$_2$CH(OH)CH$_2$CO$_2$Li)

4.87 (2H, m, ArCH$_2$OP(CH$_3$)—)

6.90–7.20 (5H, m, aromatic H's)

EXAMPLE 4

(S)-4-[[[2,4-Dichloro-6-[(4-fluorophenyl)methoxy]phenyl]methoxy]methoxyphosphinyl]-3-hydroxybutanoic acid, monolithium salt A. 2,4-Dichloro-6-(4-fluorophenylmethoxy)benzaldehyde Ref.: J. Med Chem., 1986, 29, 167)

A solution of 13.77 g (72.5 mmol) of 4,6-dichloro-2-hydroxybenzaldehyde in 100 ml of DMF was stirred and 12.02 g (87 mmol) of $K_2CO_3$ was added. This mixture was heated to ~70° C. for 60 minutes, then 11.7 ml of 4-fluorobenzyl bromide was added. The resulting solution was stirred at 70° C. for 3.5 hours, then this was poured onto ice $H_2O$ (1.5 l), filtered and washed with $H_2O$, and recrystallized from $Et_2O$/petroleum ether. Yield: 17.88 g (83%) of off-white crystals, m.p. 107°–108° C.

B. 2,4-Dichloro-6-[(4-fluorophenyl)methoxy]benzenemethanol

Cold (0° C., ice bath), dry $Et_2O$ (10.0 ml) was treated with LiAlH$_4$ (158 mg, 4.16 mmole, 0.6 eq.) and the grey suspension treated dropwise with a solution of Part A aldehyde (2.06 g, 6.93 mmole) in 10 ml dry THF. The mixture was warmed to room temperature and stirred for an hour under argon. The mixture was cooled back to 0° C. (ice bath) and quenched by sequential dropwise addition of $H_2O$ (160 μl), 15% NaOH (160 μl) and $H_2O$ (475 μl). Precipitated salts were removed by filtration through anhydrous $Na_2SO_4$ over packed Celite (¼" bed). The clear filtrate was evaporated to give 2.052 g (98.9%) of crude alcohol as white crystals. One trituration with cold hexane afforded 1.892 g (91.2%) of pure title alcohol as a white crystalline solid with m.p.=72°–73° C.

TLC (4:1) Hex-acetone, Rf=0.31, Uv and PMA.

Anal Calcd for $C_{14}H_{11}O_2Cl_2F$ (MW 301.142): C, 55.84; H, 3.68; Cl, 23.55; F, 6.31. Found: C, 55.97; H, 3.71; Cl, 23.42; F, 6.30.

C. (S)-4-[[[2,4-Dichloro-6-[(4-fluorophenyl)methoxy]phenyl]methoxy]methoxyphosphinyl]-3-t-butyldiphenylsilyloxybutanoic acid, methyl ester A solution of the Example 1 Part E(6) methyl ester (~3.84 mmole) in dry $CH_2Cl_2$ (10 ml) was treated with distilled trimethylsilyl diethylamine (1.46 ml, 7.68 mmole, 2.0 eq.) and the resulting solution stirred at room temperature under argon for 1.0 hour. The mixture was evaporated in vacuo, chased with benzene (1×20 ml) and dried in vacuo to give crude silylated phosphonic acid mono methyl ester as a colorless oil.

A solution of the crude ester (~3.84 mmole) in dry $CH_2Cl_2$ (10 ml) and dry DMF (1 drop) was cooled to −10° C. (salt, ice bath) and treated dropwise with distilled oxalyl chloride (368 μl, 4.22 mmole, 1.1 eq.). Gas evolution was evident from the clear yellow mixture. The mixture was stirred at room temperature under argon for one hour, evaporated in vacuo, chased with benzene (2×20 ml) to give crude phosphonochloridate as a viscous yellow oil.

The crude phosphonochloridate (~3.84 mmole) in dry $CH_2Cl_2$ (10 ml) at 0° C. (ice bath) was treated with Part B alcohol (1.15 g, 3.84 mmole, 1.0 eq.) followed by $Et_3N$ (805 μl, 5.76 mmole, 1.5 eq.) and 4-DMAP (47 mg, 0.384 mmole, 0.1 eq.) and the brown mixture stirred overnight at room temperature under argon. The mixture was partitioned between 5% $KHSO_4$ and EtOAc, the organic phase washed with brine, dried over anhydrous $Na_2SO_4$ and evaporated to give 3.197 g of a dark brown oil. The crude product was purified by flash chromatography on silica gel (160 g) eluting with 7:3) Hex-EtOAc. Product fractions were combined and evaporated to give 594 mg (21.1%) of desired title phosphonate as a yellow oil. Additionally, 688 mg (52.4% corrected yield) of starting Part B alcohol was recovered. TLC (1:1) Hex-acetone, Rf=0.29, UV and PMA.

D. (S)-4-[[[2,4-Dichloro-6-[(4-fluorophenyl)methoxy]phenyl]methoxy]methoxyphosphinyl]-3-hydroxy butanoic acid, methyl ester A solution of the Part C silyl ester (578 mg, 0.788 mmole) in dry THF (8 ml) was treated with glacial HOAc (180 μl, 3.2 mmole, 4.0 eq.) followed by 1.0M solution of n-$Bu_4NF$ in THF (2.36 ml, 2.36 mmole, 3.0 eq.) and the resulting pale yellow solution stirred overnight under argon at room temperature. The mixture was poured into cold $H_2O$ and extracted with EtOAc (2×). The organic phase was washed with saturated $NaHCO_3$ and brine, dried over anhydrous $Na_2SO_4$ and evaporated to give 625 mg of a yellow oil. The crude product was purified by flash chromatography on silica gel (31 g) eluting with (7:3) Hexane-acetone. Product fractions were combined and evaporated to give 339 mg (86.9%) of desired title alcohol as a clear, colorless, viscous oil. TLC (1:1) Hex-acetone, Rf=0.25, UV and PMA.

E. (S)-4-[[[2,4-Dichloro-6-[(4-fluorophenyl)methoxy]phenyl]methoxy]methoxyphosphinyl]-3-hydroxybutanoic acid, monolithium salt A solution of the Part D phosphonate (132 mg, 0.267 mmole) in dioxane (2.5 ml) was treated with 1.0N LiOH (0.32 ml, 1.2 eq.) and the mixture stirred under argon at room temperature for 4.0 hours. A white precipitate was noted. The mixture was diluted with $H_2O$, filtered and the filtrate evaporated to dryness in vacuo. The residue was chromatographed on HP-20 resin (100 ml bed) eluting with a $H_2O/CH_3CN$ linear gradient system. Product fractions were combined and evaporated, taken up in $H_2O$, filtered through a 0.4 μm polycarbonate membrane and lyophilized to give 108 mg (79% based on hydrate weight) of desired title lithium salt as a white solid.

TLC (20:1:1) $CH_2Cl_2$—$CH_3OH$—HOAc, Rf=0.41, UV and PMA.

Anal Calcd for $C_{19}H_{18}O_7Cl_2FLi_2P + 1.42$ moles $H_2O$ (MW 511.72): C, 44.59; H, 4.10; Cl, 13.86; F, 3.71; P, 6.05. Found: C, 44.22; H, 4.09; Cl, 13.91; F, 3.72; P, 6.11.

$H^1$ NMR (400 MHz):

δ 1.98–2.11 ppm (2H, m, OP(OCH₃)$\underline{CH_2}$CH(OH)—, with P=O)

2.26–2.45 ppm (2H, m, —CH(OH)$\underline{CH_2}$CO₂Li)

3.63 & 3.62 (3H, 2 doublets, 2 diastereomers, OP(OCH₃)CH₂—, $J_{HP}$—11 Hz)

4.23 (1H, m, (—CH₂$\underline{CH}$(OH)CH₂CO₂Li)

5.16 (2H, s, F—PhCH₂O)

5.24 (2H, d, ArCH₂OP, $J_{HP}$ = 6.2 Hz)

7.13–7.53 (6H, m, aromatic H's)

EXAMPLE 5

(3S)-4-[[[2,4-Dichloro-6-[(4-fluorophenyl)methoxy]phenyl]methoxy]hydroxyphosphinyl]-3-hydroxybutanoic acid, dilithium salt A mixture of the Example 4 Part D diester (210 mg, 0.424 mmole) in dioxane (4.0 ml) was treated with 1.0N LiOH (1.30 ml, 3.0 eq.) and the colorless solution heated at 50° C. (oil bath) under argon for 3.5 hours. A white precipitate was evident after 15 minutes. The mixture was diluted with $H_2O$, filtered and the filtrate evaporated in vacuo. The residue was dissolved in a minimum amount of $H_2O$ and chromatographed on HP-20 resin (100 ml bed) eluting with a $H_2O/CH_3CN$ linear gradient. Product fractions were combined and evaporated. The residue was taken up in $H_2O$ (50 ml), filtered through a 0.4 μm polycarbonate membrane and lyophilized to give 175 mg (81% based on hydrate weight) of desired title dilithium salt as a white solid.

TLC (8:1:1) $CH_2Cl_2$—$CH_3OH$—HOAc, Rf=0.07, UV and PMA.

Anal Cacld for $C_{18}H_{16}O_7Cl_2FLi_2P + 1.70$ moles $H_2O$ (MW 509.62): C, 42.42; H, 3.84; F, 3.73; Cl, 13.91; P, 6.08. Found: C, 42.46; H, 3.90; F, 3.93; Cl, 13.42; P, 5.66.

$H^1$NMR (400 MHz):

δ 1.73–1.92 ppm (2H, m, —OP(OLi)—CH₂CH(OH)—)

2.27 (1H, dd, —CH(OH)$\underline{CH_2}$CO₂Li, $J_{HH}$ = 8.8 Hz)

2.39 (1H, dd, —CH(OH)$\underline{CH_2}$CO₂Li, $J_{HH}$ = 4.4 Hz)

4.26 (1H, m, CH₂$\underline{CH}$(OH)CH₂CO₂Li)

5.08 (2H, s, F-Ph-CH₂OAr)

7.03–7.53 (6H, m, aromatic H's).

EXAMPLE 6

(3S)-4-[[2,4-Dichloro-6-[(4-fluorophenyl)methoxy]-phenyl]methoxy]methylphosphinyl]-3-hydroxybutanoic acid, methyl ester A. (S)3-[[(1,1-Dimethylethyl)diphenylsilyl]oxy]-4-(ethoxymethylphosphinyl)butanoic acid, methyl ester A mixture of the Example 1 Part E(3) iodide (4.68 g, 9.18 mmole) in methyl diethoxyphosphine (Strem Chemicals, 5.0 g, 36.7 mmole) was heated at 100° C. (oil bath) for 2.5 hours, then at 150° C. for three additional hours under argon. A white precipitate slowly formed in the yellow solution. Excess phosphine was distilled off in vacuo (0.5 mm Hg) and the crude product purified by flash chromatography on silica gel eluting with (65:35) Hexane-acetone. Product fractions were combined and evaporated to give 1.590 g (38%) of desired title phosphinic ester (mixture of diastereomers) as a clear viscous oil. TLC (3:2) Hex-acetone, Rf (2 diastereomers)=0.19 and 0.22, UV and PMA.

B. (3S)-4-[[2,4-Dichloro-6-[(4-fluorophenyl)methoxy]phenyl]methoxy]methylphosphinyl]-3-t-butyldiphenylsilylbutanoic acid, methyl ester A solution of Part A phosphinic ester (605 mg, 1.3 mmole) in dry $CH_2Cl_2$ (6.0 ml) was treated with bis(trimethylsilyl)trifluoroacetamide (BSTFA) (280 µl, 1.05 mmole, 0.8 eq.) and trimethylsilyl bromide (TMSBr) (210 µl, 1.57 mmole, 1.2 eq.) and the resulting solution stirred at room temperature under argon overnight. 5% $KHSO_4$ (15 ml) was added and the mixture extracted with EtOAc. The organic phase was washed with brine, dried over anhydrous $Na_2SO_4$ and evaporated in vacuo to give crude phosphinic acid as a colorless oil.

A solution of the crude phosphinic acid (~1.3 mmole) in dry $CH_2Cl_2$ (6.0 ml) was treated with distilled trimethylsilyl diethylamine (270 µl, 1.44 mmole, 1.1 eq.) and the clear mixture was stirred at room temperature under argon for 1.0 hour. The mixture was evaporated in vacuo, chased with benzene (1×15 ml), and dried in vacuo.

A cooled (0° C., ice bath) solution of the crude silylated phosphinic acid (~1.3 mmole) in dry $CH_2Cl_2$ (6.0 ml) and DMF (1 drop) was treated dropwise via syringe with distilled oxalyl chloride (130 µl, 1.44 mmole, 1.1 eq.). Gas evolution was evident. The mixture was stirred at room temperature under argon for one hour then evaporated in vacuo, chased with benzene (2×15 ml) and dried in vacuo to give crude phosphinochloridate as a yellow oil.

A cooled (0° C., ice bath) solution of phosphinochoridate (~1.3 mmole) and Example 1 Part E(6) alcohol (392 mg, 1.3 mmole) in dry $CH_2Cl_2$ (6.0 ml) was treated with $Et_3N$ (275 µl, 1.97 mmole, 1.5 eq.) and 4-DMAP (16 mg, 0.13 mmole, 0.1 eq) and the resulting yellow mixture stirred under argon at room temperature overnight. The mixture was partitioned between 5% $KHSO_4$ and EtOAc, the organic phase washed with brine, dried over anhydrous $Na_2SO_4$ and evaporated to give 908 mg of crude product as a dark yellow oil. The crude product was purified by flash chromatography on silica gel (45 g) eluting with (3:2) Hex-EtOAc. Product fractions wee combined and evaporated to give 266 mg (28.3%) of desired title product as a clear, colorless oil. Also 197 mg (57%, corrected yield) of the starting alcohol was recovered.

C. (3S)-4-[[2,4-Dichloro-6-[(4-fluorophenyl)methoxy]phenyl]methoxy]methylphosphinyl]-3-hydroxybutanoic acid, methyl ester A solution of the Part B silyl ester (275 mg, 0.38 mole) in dry THF (6.0 ml) was treated with glacial HOAc (90 µl, 1.53 mmole, 4.0 eq.) and a 1.0M solution in THF of tetrabutylammonium fluoride (1.2 ml, 3.1 eq.). The resulting solution was stirred overnight under argon at room temperature. The mixture was partitioned between cold $H_2O$ and EtOAc, the organic phase washed with saturated $NaHCO_3$ and brine, dried over anhydrous $Na_2SO_4$ and evaporated to give 258 mg of a yellow oil. The crude product was purified by flash chromatography on LPS-1 silica gel (8 g) eluting with (1:1) Hexane-acetone. Product fractions were combined and evaporated to give 142 mg (77%) of desired title alcohol as a clear, colorless, oil. TLC (1:1) Hexane-acetone, Rf=0.20, UV and PMA.

D. (3S)-4-[[2,4-Dichloro-6-[(4-fluorophenyl)methoxy]phenyl]methoxy]methylphosphinyl]-3-hydroxybutanoic acid, monolithium salt A solution of the Part C methyl ester (142 mg, 0.296 mmole) in dioxane (3.0 ml) was treated with 1.0N LiOH (0.36 ml, 1.2 eq.) and the resulting white suspension stirred under argon at room temperature for 2.0 hours. The mixture was diluted with $H_2O$, filtered through a 0.4 µm polycarbonate membrane and the filtrate evaporated in vacuo.

The crude product was dissolved in a minimum amount of $H_2O$ and chromatographed on a 100 ml bed of HP-20 resin eluting with a $H_2O/CH_3CN$ linear gradient. Product fractions were combined and evaporated. The residue was taken up in $H_2O$, filtered through a polycarbonate membrane and lyophilized to give 93 mg (63% based on hydrate weight) of desired title lithium salt as a white solid.

TLC (8:1:1) $CH_2Cl_2$— $CH_3OH$—HOAc, Rf=0.51, UV and PMA.

Anal Calcd for $C_{19}H_{19}O_7Cl_2FLiP + 1.38$ moles $H_2O$ (MW 495.94): C, 46.01; H, 4.42; F, 3.83; Cl, 14.30; P, 6.24. Found: C, 46.10; H, 4.49; F, 3.82; Cl, 14.32; P, 6.43.

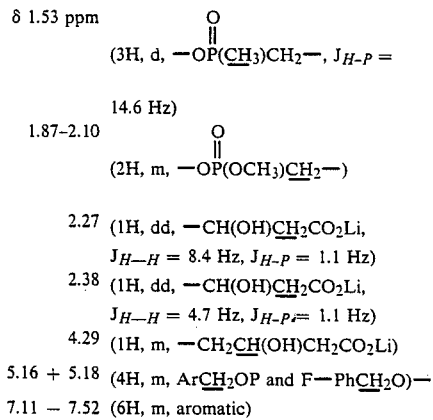

EXAMPLE 7

(S)-4-[[[4'-Fluoro-3,3',5-trimethyl[1,1'-biphenyl-2-yl]methyl]amino]methoxyphosphinyl]-3-hydroxybutanoic acid, monolithium salt A. 4'-Fluoro-3,3',5-trimethyl[1,1'-biphenyl]-2-carboxylic acid A solution of the Example 1 Part C(2) aldehyde (1.0 g, 4.13 mmole) in acetone (10.0 ml) at 0° C. (ice bath) was treated dropwise with 8.0N Jones reagent (4.1 ml, excess) and the resulting brown-green suspension stirred overnight under argon at room temperature. Excess oxidant was destroyed by adding isopropanol (10.0 ml) and precipitated chromium salts removed by filtration through a ¼" pad of Celite. The filtrate was evaporated, taken up in EtOAc, washed with 1.0N HCl (2×), saturated $NH_4Cl$ (2×) and brine, then dried over anhydrous $Na_2SO_4$ and evaporated to give 1.011 g of a green solid with m.p. 153°–154° C.

The crude acid was purified via the dicyclohexylamine salt. To a solution of the crude acid in EtOAc (5.0 ml) was added dicyclohexyl amine (DCHA) (823 μl, 1.0 eq.). The solution diluted with hexane and precipitated crystalline salt was collected to give 997 mg (55% from aldehyde, m.p. 181°–183° C.) of desired product as an off-white crystalline DCHA salt.

The title free acid was regenerated from the DCHA salt by partitioning the salt between 5% $KHSO_4$ and EtOAc. The organic phase was washed with brine, dried over anhydrous $Na_2SO_4$ and evaporated in vacuo to give 554 mg (52% from aldehyde) of desired title acid. TLC (9:1) $CH_2Cl_2$—$CH_3OH$, Rf=0.37, UV and PMA.

B. 4'-Fluoro-3,3',5-trimethyl[1,1'-biphenyl]-2-carboxamide

A solution of the Part A acid (554 mg, 2.14 mmole) in dry $CH_2Cl_2$ (6.0 ml) and dry DMF (1 drop) at 0° C. (ice bath) was treated dropwise via syringe with distilled oxalyl chloride (205 μl, 2.35 mmole, 1.1 eq.) and the clear yellow solution stirred under argon at room temperature for one hour. The mixture was evaporated in vacuo, chased with benzene (2×) and dried in vacuo to give crude acid chloride as a yellow oil.

A cooled (0° C., ice bath) mixture of THF (3.0 ml) and concentrated $NH_4OH$ (2.0 ml, excess) was treated dropwise with a THF solution (3.0 ml) of the crude acid chloride and the bright orange solution stirred at room temperature under argon for 1.0 hour. The mixture was partitioned between $H_2O$ and EtOAc, the organic phase washed with saturated $NaHCO_3$, $H_2O$ and brine, then dried over anhydrous $Na_2SO_4$ and evaporated to give 528 mg (96.1%) of crude amide as a light orange solid. One recrystallization from EtOAc-hexane afforded 435 mg (79.1%) of purified title amide as pale yellow needles with m.p. 197°–198° C. The TLC (1:1) $Et_2O$-Acetone Rf=0.83, UV and PMA.

C. 4'-Fluoro-3,3',5-trimethyl[1,1'-biphenyl]-2-methanamine

A cooled (0° C., ice bath) solution of dry THF (5.0 ml) was treated with solid $LiAlH_4$ (125 mg, 3.3 mmole) and the gray suspension treated dropwise over five minutes with a solution of the Part B amide (424 mg, 1.65 mmole) in THF (5.0 ml). The resulting suspension was stirred at room temperature under argon for 2.5 hours, then refluxed for 45 minutes. The mixture was cooled to 0° C. (ice bath) and quenched by sequential dropwise addition of 125 μl $H_2O$, 125 μl of 15% NaOH and 375 μl $H_2O$. Precipitated aluminum salts were removed by filtration through anhydrous $Na_2SO_4$ over packed Celite. The clear filtrate was evaporated in vacuo to give the crude amine as a clear oil. TLC (7:3) $Et_2O$-acetone, Rf=0.60, UV and PMA. The amine was purified as the HCl salt.

A solution of the crude amine (~1.65 mmole) in absolute EtOH (8.0 ml) was treated with concentrated HCl (152 μl, 1.82 mmole) and the mixture stirred for 15 minutes at room temperature under argon. The mixture was evaporated in vacuo to a white crystalline solid. The solid was triturated with cold $Et_2O$, collected by filtration and dried in vacuo to give 426 mg (92.4%) of title amine-HCl as fine white crystals.

D. (S)-4-[[[[4'-Fluoro-3,3',5-trimethyl[1,1'-biphenyl]-2-yl]methyl]amino]methoxyphosphinyl]-3-t-butyldiphenylsilyloxy butanoic acid, methyl ester A solution of Example 1 Part E(6) methyl ester (~2.0 mmole) in dry $CH_2Cl_2$ (5.0 ml) was treated with distilled trimethylsilyl diethylamine (758 μl, 4.0 mmole, 2.0 eq.) and the clear mixture stirred at room temperature under argon for one hour. The mixture was evaporated in vacuo, chased with benzene (1×15 ml) and dried in vacuo.

A cooled (0° C.) solution of the crude silyl phosphonate in dry $CH_2Cl_2$ (7.0 ml) and DMF (1 drop) was treated dropwise with distilled oxalyl chloride (192 μl, 2.2 mole, 1.1 eq.). Gas evolution was evident from the clear yellow mixture. The solution was stirred at room temperature for one hour, evaporated in vacuo, chased with benzene (2×15 ml), and dried in vacuo to give the crude phosphonochloridate as a yellow, viscous oil.

A cooled (0° C.) solution of the phosphonochloridate and Part C biphenyl amine·HCl (416 mg, 1.49 mmole) in dry $CH_2Cl_2$ (10 ml) was treated with $Et_3N$ (641 μl, 4.6 mmole, 2.3 eq.) and 4-DMAP (24 mg, 0.2 mmole, 0.1 eq.) and the clear yellow mixture stirred overnight at room temperature under argon. The mixture was partitioned between 5% $KHSO_4$ and EtOAc, the organic phase washed with brine, dried over anhydrous $Na_2SO_4$ and evaporated in vacuo to give 1.19 g of a yellow oil. The crude product was purified by flash chromatography on silica gel (60 g) eluting with (7:3) hexane-acetone. Product fractions were evaporated to give 588 mg (59.5%) of desired title phosphonamide as a pale yellow, viscous oil.

TLC (7:3) Hexane-acetone, Rf=0.20, UV and PMA.

E. (S)-4-[[[[4'-Fluoro-3,3',5-trimethyl[1,1'-biphenyl)-2-yl]methyl]amino]methoxyphosphinyl]-3-hydroxybutanoic acid, methyl ester A solution of Part D silyl ether (588 mg, 0.888 mmole) in dry THF (10.0 ml) was treated with glacial HOAc (203 μl, 3.55 mmole, 4.0 eq.) and a 1.0M solution in THF of tetrabutylammonium fluoride (2.66 ml, 2.66 mmole, 3.0 eq.) and the resulting solution stirred overnight under argon at room temperature. The mixture was poured into cold $H_2O$ and extracted with EtOAc. The organic phase was washed with saturated $NaHCO_3$ and brine, then dried over anhydrous $Na_2SO_4$ and evaporated in vacuo to give 605 mg of an orange oil. The crude product was purified by flash chromatography on silica gel (36 g) eluting with (1:1) Hexaneacetone. Product fractions were combined and evaporated to give 196 mg (50.4%) of desired title alcohol as a light orange oil.

TLC (1:1) Hexane-acetone, Rf=0.16, UV and PMA.

F. (S)-4-[[[[4'-Fluoro-3,3',5-trimethyl[1,1'-biphenyl]-2-yl]methyl]amino]methoxyphosphinyl]-3-hydroxybutanoic acid, monolithium salt A solution of the Part E diester (105 mg, 0.240 mmole) in dioxane (2.0 ml) was treated with 1.0N LiOH (288 μl, 1.2 eq.) and the white suspension stirred under argon at room temperature for 4.0 hours. The mixture was diluted with $H_2O$, filtered, the filtrate evaporated in vacuo. The residue was chromatographed on HP-20 (100 ml bed) resin eluting with a $H_2O/CH_3CN$ linear gradient. Product fractions were combined and evaporated. The residue was taken up in $H_2O$ (50 ml), filtered through a 0.4 μm polycarbonate membrane and lyophilized to give 70 mg (62.7% based on weight of hydrate) of desired title lithium salt as a white solid.

TLC (20:1:1) $CH_2Cl_2$—$CH_3OH$—HOAc, Rf=0.19, UV and PMA.

Anal Calcd for $C_{21}H_{26}NO_5PFLi+2.41$ moles $H_2O$ (MW 472.75): C, 53.35; H, 6.57; N, 2.96; F, 4.02; P, 6.55. Found: C, 53.35; H, 6.52; N, 2.98; F, 4.05; P, 6.59.

| $H^1$ NMR (400 MHz): | |
|---|---|
| δ 1.79–1.97 ppm | (2H, m, —P(OCH₃)CH₂—), O double bond |
| 2.26–2.44 ppm | (2H, m, —CH₂CO₂Li) |
| 2.29 | (3H, s, aromatic methyl) |
| 2.31 | (3H, d, aromatic methyl α to fluorine, $J_{HF}$ = 1.4 Hz) |
| 2.47 | (3H, aromatic methyl) |
| 3.46 & 3.50 | (3H, 2 doublets, 2 diastereomers, $J_{HP}$ = 10.5 Hz) |
| 3.96 | (2H, m, —PhCH₂NHP(OCH₃)—), O double bond |
| 4.71 | (1H, m, (—CH₂CH(OH)CH₂CO₂Li) |
| 6.84–7.21 | (5H, m, aromatic protons) |

EXAMPLES 8 and 20

Following the procedures as outlined heretofore and as described in the previous working Examples, the following additional compounds may be prepared.

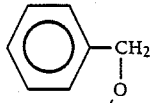

| Ex. No. | R | Z | n | X | $R^x$ |
|---|---|---|---|---|---|
| 8. | OH | 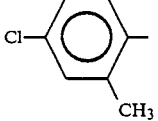 | 1 | O | H |
| 9. | $C_2H_5O$ | 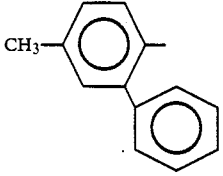 | 2 | NH | $CH_3$ |
| 10. | $C_3H_7$ | 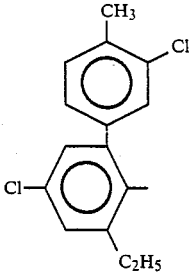 | 1 | O | Li |

-continued
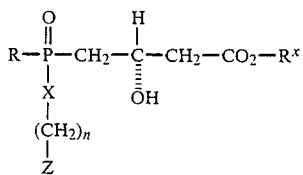
| Ex. No. | R | Z | n | X | R$^x$ |
|---|---|---|---|---|---|
| 11. | CH$_3$O | 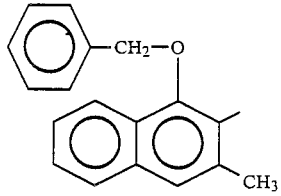 | 2 | NH | H |
| 12. | OH | 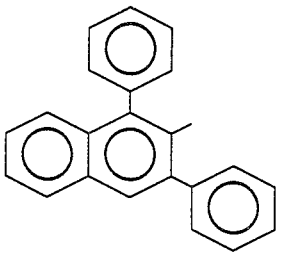 | 2 | O | H |
| 13. | C$_4$H$_9$O | 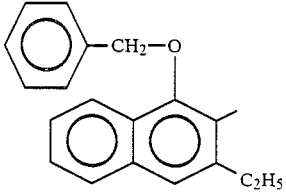 | 1 | O | Li |
| 14. | C$_5$H$_{11}$ | 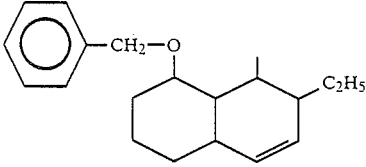 | 1 | NH | CH$_3$ |
| 15. | OK | 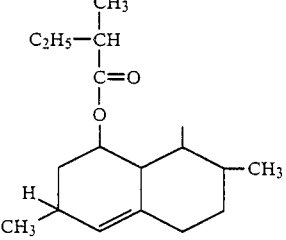 | 2 | O | OK |
| 16. | ONa | 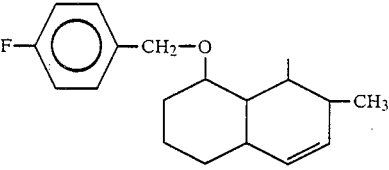 | 2 | O | H |

-continued

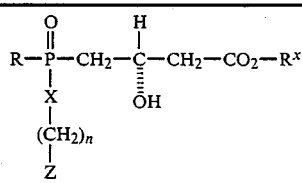

| Ex. No. | R | Z | n | X | R$^x$ |
|---|---|---|---|---|---|
| 17. | CH$_3$O | (4-F-phenyl)-CH$_2$-O-decalin with CH$_3$, HO, H substituents | 1 | NH | H |
| 18. | CH$_3$ | C$_2$H$_5$-C(CH$_3$)$_2$-C(=O)-O-decalin with CH$_3$, OH substituents | 1 | O | H |
| 19. | HO | phenyl | 2 | O | Li |
| 20. | CH$_3$O | tetraphenyl group | 1 | NH | H |

EXAMPLES 21

(S)-4-Diisoproplyoxyphosphinyl)-3-[[(1,1-dimethylethyl)diphenylsilyl]oxy]-butanoic acid, methyl ester The Example 1 Part E(3) iodide (45.1 mmol., 21.70 g) was stirred under high vacuum for 30 minutes. Freshly distilled triisopropyl phosphite (0.451 mol., 93.92 g, 113.37 ml.) was added in one portion and the reaction mixture was stirred under argon and heated in a 155° C. oil bath for 16.5 hours. The mixture was then cooled to room temperature. Excess triisopropyl phosphite and volatile reaction products were removed by short path distillation (10 mm Hg) followed by Kugelrohr distillation (0.50 mm Hg, 100° C., 8 hours). The product was further purified via flash chromatography (95 mm diam. column, 6"/Merck. silica gel, 6/3/1 Hexane/acetone/toluene eluent, 2"/min flow rate, 50 ml fractions) to afford 17.68 g (33.96 mmol, 75% yield) of the title isopropylphosphonate as a clear viscous oil.

TLC: Silica gel R$_f$=0.32 (6:3:1 Hexane/acetone toluene).

| $^1$HNMR | (270 MHz, CDCl$_3$) |
|---|---|
| δ | 7.70–7.65 (m,4H) |
| | 7.45–7.35 (m,6H) |
| | 4.57–4.44 (m,3H) |
| | 3.59 (s,3H) |
| | 2.94 and 2.88 (2 × d, 1H J = 3.7 Hz) |
| | 2.65 and 2.60 (2 × d, 1H J = 7.4 Hz) |
| | 2.24–1.87 (Series of m, 2H) |
| | 1.19 and 1.12 (2 × d, 12H J = 6.3 Hz) |
| | 1.01 (s, 9H) |

EXAMPLE 22

(S)-4-(Hydroxymethoxyphosphinyl)-3-[[(1,1-dimethylethyl)diphenylsilyl]oxy]butanoic acid, methyl ester, dicyclohexylamine (1:1) salt The Example 21 isopropyl phosphonate (30.5 mmol, 10.66 g) was stirred under argon, at room temperature, in 80 ml of dry CH$_2$Cl$_2$. This solution was treated dropwise (5 min) with bistrimethylsilyltrifluoroacetamide (BSTFA) (32.8 mmol, 8.44 g, 8.71 ml), followed by dropwise addition (10 min) of trimethylsilylbromide (TMSBr) (51.3 mmol, 7.84 g, 6.75 ml). After stirring at room temperature for 20 hours, the reaction mixture was quenched with 200 ml of 5% aqueous KHSO$_4$ and stirred vigorously for 15 minutes. The aqueous layer was extracted 3 times with ethylacetate. The organic extracts were combined, washed once with brine, dried over Na₂SO₄ and concentrated in vacuo. The residue was azeotroped 2 times with 50 ml of toluene. The precipitate which formed was suspended in toluene and filtered. The filtrate was concentrated and the azeotrope/filter process repeated. The resulting filtrate was evaporated in vacuo and then pumped under high vacuum for 5 hours. The resulting viscous clear oil was stirred under argon, at room temperature, in 50 ml of dry pyridine. This solution was treated in one portion with dicyclohexylcarbodiimide (DCC) (22.6 mmol, 4.65 g), followed by addition of methanol (41.0 mmol, 1.31 g, 1.67 ml). After stirring at room temperature for 20 hours, the reaction mixture was filtered through a celite pad in a sintered glass funnel. The celite was washed with ethyl acetate and the combined filtrates were evaporated in vacuo. The residue was redissolved in ethyl acetate and washed 2 times with 5% aqueous KHSO₄ and once with brine. The organic extract was dried over Na₂SO₄, filtered, the filtrate concentrated and azeotroped 2 times with toluene, suspended in toluene and filtered. The resulting filtrate was again concentrated, azeotroped, filtered and the filtrate evaporated in vacuo and placed under high vacuum for 6 hours to afford the phosphonate monoester as a clear viscous oil (10.2 g, ≦100% yield). TLC: silica gel $R_f$=0.50 (7:2:1 nPrOH/NH₄OH/H₂O). The phosphonate monoester [1.21 g was pumped under high vacuum for 4 hours, affording 1.16 g (2.57 mmol)] was dissolved in 10 ml of dry ethyl ether and treated dropwise with dicyclohexylamine (2.65 mmol, 0.481 g, 0.528 ml). The resulting homogeneous solution sat at room temperature for 7 hours resulting in significant crystal formation. The mixture was stored at −20° C. for 16 hours and then warmed to room temperature and filtered. The crystals were washed with cold, dry ethyl ether and then pumped under high vacuum over P₂O₅ for 18 hours. The crystals were subsequently pumped under high vacuum at 45° C. for 4 hours, affording 1.25 g (1.98 mmol, 77% yield) of the title dicyclohexylamine salt as a white powdery solid, m.p. 155°–156° C.

| TLC: Silica gel $R_f$ =0.57 (20% MeOH/CH₂Cl₂) ¹H NMR: (270 MH₂, CDCl₃) |
|---|
| 7.71–7.65 (m, 4H) |
| 7.40–7.32 (m, 6H) |
| 4.02 (m, 1H) |
| 3.52 (s, 3H) |
| 3.28 and 3.22 (m, 1H) |
| 3.11 (d, 3H J = 11 Hz) |
| 2.77–2.64 (m, 2H) |
| 2.62–2.56 (m, 1H) |
| 1.92–1.08 (Series of m, 22H) |
| 1.00 (S. 9H) |

Mass Spec: (FAB) 632 (M&H)+.

IR: (KBr) 3466–3457 (broad), 3046, 3016, 2997, 2937, 2858, 2836, 2798, 1855 2721, 2704, 2633, 2533, 2447, 1736, 1449, 1435, 1426, 1379, 1243, 1231, 1191, 1107, 1074, 1061, 1051, 820 CM−1.

Anal Calcd for C₂₂H₃₁ O₆PSi.C₁₂H₂₃N: C,64.63; H,8.61; N,2.22. Found C, 64.51; H, 8.49; N, 2.18.

What is claimed is:
1. A compound of the structure

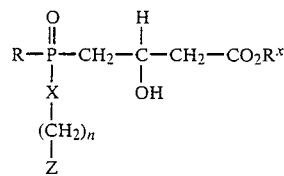

including salts thereof, wherein R is OH, lower alkoxy or lower alkyl;
$R^x$ is H or lower alkyl:
X is —O— or —NH—;
n is 1 or 2
Z is a hydrophobic anchor which is

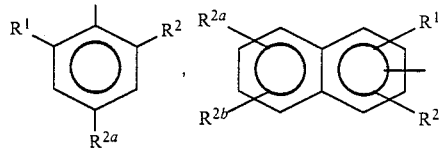

or

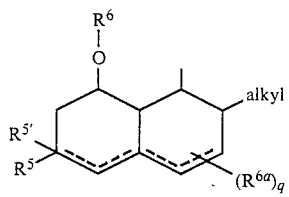

wherein the dotted lines represent optional double bonds,
wherein $R^1$, $R^2$, $R^{2a}$ and $R^{2b}$ may be the same or different and are H, halogen, lower alkyl, haloalkyl, phenyl, substituted phenyl or $OR^Y$ in which $R^Y$ is H, alkanoyl, benzoyl, phenyl, halophenyl, phenyl-lower alkyl, lower alkyl, cinnamyl, haloalkyl, allyl, cycloalkyl-lower alkyl, adamantyl-lower alkyl or substituted phenyl-lower alkyl;
wherein Z is

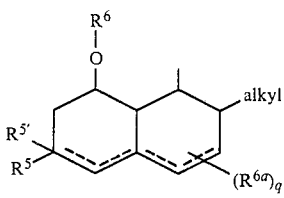

$R^5$ and $R^{5'}$ are the same or different and are H, lower alkyl or OH, one or $R^5$ and $R^{5'}$ being present when the carbon to which it is attached is linked to a double bond;
$R^6$ is

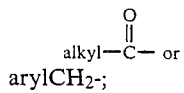

$R^{6a}$ is lower alkyl, hydroxy, oxo or halogen, and q is 0, 1, 2 or 3,
wherein $R^x$ is hydrogen or lower alkyl in free acid form or in the form of a physiologically-hydrolysable and -acceptable ester in salt form.

2. A method of inhibiting cholesterol biosynthesis which comprises administering to a patient in need of such treatment an effective cholesterol biosynthesis inhibiting amount of a compound as defined in claim 1.

3. A hypocholesterolemic or hypolipemic composition comprising a compound as defined in claim 1 and a pharmaceutically acceptable carrier therefor.

4. The compound as defined in claim 1 wherein X is —O—.

5. The compound as defined in claim 1 wherein R is alkoxy.

6. The compound as defined in claim 1 wherein Z is

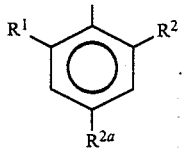

7. The compound as defined in claim 5 wherein Z is

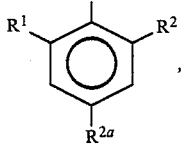

R is alkoxy, and $R^1$ is phenyl or benzyloxy, $R^2$ and $R^{2a}$ are the same of different and are halogen or lower alkyl, $(CH_2)_n$ is $CH_2$ and R is methoxy.

8. The compound as defined in claim 7 wherein $R^1$ is halo-benzyloxy or alkyl(halo)phenyl.

9. The compound as defined in claim 1 having the name (S)-4-[[[4'-fluoro-3,3',5-trimethyl[1,1'-biphenyl]-2-yl]methoxy]methoxyphosphinyl]-3-hydroxy-butanoic acid, methyl ester or its monolithium salt.

10. The compound as defined in claim 1 having the name (S)-4-[[[4'-fluoro-3,3',5-trimethyl[1,1'-biphenyl]-2-yl]methoxy]hydroxyphosphinyl]-3-hydroxybutanoic acid, dilithium salt.

11. The compound as defined in claim 1 having the name (3S)-4-[[[4'-fluoro-3,3', 5-trimethyl[1,1'-biphenyl]-2-yl]methoxy]methylphosphinyl]-3-hydroxybutanoic acid, monolithium salt.

12. The compound as defined in claim 1 having the name (S) -4-[[[2,4-dichloro-6-[(4-fluorophenyl)methoxy]phenyl]methoxy]methoxyphosphinyl]-3-hydroxybutanoic acid, monolithium salt.

13. The compound as defined in claim 1 having the name (3S)-4-[[[2,4-dichloro-6-[(4-fluorophenyl)methoxy]phenyl]methoxy]hydroxyphosphinyl]-3-hydroxybutanoic acid, dilithium salt.

14. The compound as defined in claim 1 having the name (3S)-4-[[2,4-dichloro-6-[(4-fluorophenyl)methoxy]phenyl]methoxy]methylphosphinyl]-3-hydroxybutanoic acid, or its methyl ester.

15. The compound as defined in claim 1 having the name (S)-4-[[[4'-fluoro-3,3',5-trimethyl[1,1'-biphenyl-2-yl]methyl]amino]methoxyphosphinyl] -3-hydroxybutanoic acid, monolithium salt.

16. A compound useful in inhibiting the enzyme 3-hydroxy-3-methylglutaryl-coenzyme A reductase having the moiety

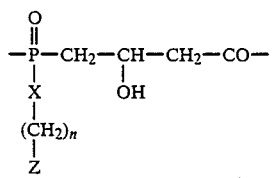

wherein X is —O— or —NH—, n is 1 or 2 and Z is a hydrophobic anchor.

17. The compound as defined in claim 16 wherein the hydrophobic anchor is a lipophilic group which when linked to the HMG-like upper side chain of the molecule by the appropriate linker (X), binds to a hydrophobic pocket of the enzyme not utilized in binding the substrate HMG CoA, resulting in enhanced potency relative to compounds where Z=H.

18. The compound as defined in claim 16 having the structure

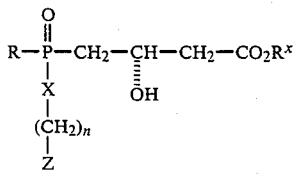

including salts thereof, wherein R is OH, lower alkoxy or lower alkyl and $R^x$ is H or lower alkyl.

19. The compound as defined in claim 1 wherein X is —NH—.

20. The compound as defined in claim 19 wherein R is alkoxy and $(CH_2)_n$ is $CH_2$.

21. The compound as defined in claim 19 wherein Z is

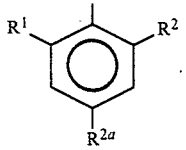

22. The compound as defined in claim 21 wherein $R^1$ is alkyl(halo)phenyl.

* * * * *